(12) United States Patent
Lee et al.

(10) Patent No.: US 7,465,705 B2
(45) Date of Patent: Dec. 16, 2008

(54) NOGO RECEPTOR ANTAGONISTS

(75) Inventors: Daniel H. S. Lee, Sudbury, MA (US); R. Blake Pepinsky, Arlington, MA (US); Weiwei Li, Staten Island, NY (US); Jane K. Relton, Belmont, MA (US); Dane S. Worley, Somerville, MA (US); Stephen M. Strittmatter, Guilford, CT (US); Dinah W. Y. Sah, Boston, MA (US); Sylvia A. Rabacchi, Glen Rock, NJ (US)

(73) Assignees: Yale University, New Haven, CT (US); Biogen Idec MA Inc., Cambridge, MA (US)

( * ) Notice: Subject to any disclaimer, the term of this patent is extended or adjusted under 35 U.S.C. 154(b) by 233 days.

(21) Appl. No.: 11/055,163

(22) Filed: Feb. 10, 2005

(65) Prior Publication Data

US 2005/0271655 A1    Dec. 8, 2005

Related U.S. Application Data

(63) Continuation of application No. PCT/US03/25004, filed on Aug. 7, 2003.

(60) Provisional application No. 60/402,866, filed on Aug. 10, 2002.

(51) Int. Cl.
*A61K 38/00* (2006.01)
*A61K 38/16* (2006.01)
*C07K 14/00* (2006.01)
*C07K 5/00* (2006.01)
*C07K 16/00* (2006.01)

(52) U.S. Cl. .................. 514/12; 514/2; 424/198.1; 530/350; 530/388.22

(58) Field of Classification Search .................. None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,399,216 A | 8/1983 | Axel et al. |
| 4,510,245 A | 4/1985 | Cousens et al. |
| 4,634,665 A | 1/1987 | Axel et al. |
| 4,816,567 A | 3/1989 | Cabilly et al. |
| 4,968,615 A | 11/1990 | Koszinowski et al. |
| 5,168,062 A | 12/1992 | Stinski |
| 5,179,017 A | 1/1993 | Axel et al. |
| 5,223,409 A | 6/1993 | Ladner et al. |
| 5,877,293 A | 3/1999 | Adair et al. |
| 5,886,152 A | 3/1999 | Nakatani et al. |
| 6,054,297 A | 4/2000 | Carter et al. |
| 6,475,753 B1 | 11/2002 | Ruben et al. |
| 6,627,741 B2 | 9/2003 | Ruben et al. |
| 6,774,216 B2 | 8/2004 | Ruben et al. |
| 7,119,165 B2 | 10/2006 | Strittmatter |
| 7,173,118 B2 | 2/2007 | Strittmatter et al. |
| 2002/0012965 A1 | 1/2002 | Strittmatter |
| 2002/0055139 A1 | 5/2002 | Holtzman et al. |
| 2002/0077295 A1 | 6/2002 | Strittmatter |
| 2003/0113325 A1 | 6/2003 | Hu et al. |
| 2003/0113326 A1 | 6/2003 | Hu et al. |
| 2003/0124704 A1 | 7/2003 | Strittmatter et al. |
| 2004/0029169 A1 | 2/2004 | Hu et al. |
| 2005/0048520 A1 | 3/2005 | Strittmatter et al. |
| 2005/0221420 A1 | 10/2005 | Barske et al. |
| 2005/0271655 A1 | 12/2005 | Lee et al. |

FOREIGN PATENT DOCUMENTS

| | | |
|---|---|---|
| EP | 0 216 846 B1 | 1/1990 |
| EP | 0 256 055 B1 | 8/1991 |
| EP | 0 323 997 B1 | 4/1993 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |

(Continued)

OTHER PUBLICATIONS

Pettit and Gombotz, 1998, TIBTECH, 16:343-349.*

(Continued)

*Primary Examiner*—Elizabeth C. Kemmerer
*Assistant Examiner*—Sandra Wegert
(74) *Attorney, Agent, or Firm*—Sterne, Kessler, Goldstein & Fox P.L.L.C.

(57) ABSTRACT

Disclosed are immunogenic Nogo receptor-1 polypeptides, Nogo receptor-1 antibodies, antigen-binding fragments thereof, soluble Nogo receptors and fusion proteins thereof and nucleic acids encoding the same. Also disclosed are compositions comprising, and methods for making and using, such Nogo receptor antibodies, antigen-binding fragments thereof, soluble Nogo receptors and fusion proteins thereof and nucleic acids encoding the same.

12 Claims, 16 Drawing Sheets

FOREIGN PATENT DOCUMENTS

| WO | WO 01/51520 A2 | 7/2001 |
|---|---|---|
| WO | WO 02/29059 A2 | 4/2002 |
| WO | WO 03/002602 A2 | 1/2003 |
| WO | WO 03/018631 A2 | 3/2003 |
| WO | WO 03/031462 A2 | 4/2003 |
| WO | WO 03/035687 A1 | 5/2003 |
| WO | WO 03/089470 A1 | 10/2003 |
| WO | WO 2004/014311 A2 | 2/2004 |
| WO | WO 2004/093893 A2 | 11/2004 |
| WO | WO 2005/016955 A2 | 2/2005 |

OTHER PUBLICATIONS

Basso, D.M., et al., "MASCIS Evaluation of Open Field Locomotor Scores: Effects of Experience and Teamwork on Reliability," *J. Neurotrauma* 13:343-359, Mary Ann Liebert, Inc. (1996).

Brittis, P.A. and Flanagan, J.G., "Nogo Domains and a Nogo Receptor: Implications for Axon Regeneration," *Neuron* 30:11-14, Cell Press (Apr. 2001).

Chen, M.S., et al., "Nogo-A is a myelin-associated neurite outgrowth inhibitor and an antigen for monoclonal antibody IN-1," *Nature* 403:434-439, Macmillan Magazines Ltd. (2000).

Domeniconi, M., et al., "Myelin-Associated Glycoprotein Interacts with the Nogo66 Receptor to Inhibit Neurite Outgrowth," *Neuron* 35:283-290, Cell Press (Jul. 2002).

Fournier, A.E., et al., "Identification of a receptor mediating Nogo-66 inhibition of axonal regeneration," *Nature* 409:341-346, Macmillan Magazines Ltd. (Jan. 2001).

Fournier, A.E., et al., "Truncated Soluble Nogo Receptor Binds Nogo-66 and Blocks Inhibition of Axon Growth by Myelin," *J. Neurosci.* 22:8876-8883, Society of Neuroscience with the assistance of Stanford University's HighWire Press™ (Oct. 2002).

Grandpré, T., et al., "Identification of the Nogo inhibitor of axon regeneration as a Reticulon protein," *Nature* 403:439-444, Macmillan Magazines Ltd. (2000).

Grandpré, T., et al., "Nogo-66 receptor antagonist peptide promotes axonal regeneration," *Nature* 417:547-551, Nature Publishing Group (May 2002).

Grimpe, B., et al., "The Critical Role of Basement Membrane-Independent Laminin γ 1 Chain during Axon Regeneration in the CNS," *J. Neurosci.* 22:3144-3160, Society for Neuroscience with the assistance of Stanford University's HighWire Press™ (Apr. 2002).

Jones, L.L., et al., "NG2 Is a Major Chondroitin Sulfate Proteoglycan Produced after Spinal Cord Injury and Is Expressed by Macrophages and Oligodendrocyte Progenitors," *J. Neurosci.* 22:2792-2803, Society for Neuroscience with the assistance of Stanford University's HighWire Press™ (Apr. 2002).

Li, M., et al, "Functional Role and Therapeutic Implications of Neuronal Caspase-1 and -3 in a Mouse Model of Traumatic Spinal Cord Injury," *Neurosci.* 99:333-342, Elsevier Science Ltd. (2000).

Li, S. and Strittmatter, S.M., "Delayed Systemic Nogo-66 Receptor Antagonist Promotes Recovery from Spinal Cord Injury," *J. Neurosci.* 23:4219-4227, Society for Neuroscience with the assistance of Stanford University's HighWire Press™ (May 2003).

Liu, B.P., et al., "Myelin-Associated Glycoprotein as a Functional Ligand for the Nogo-66 Receptor," *Science* 297:1190-1193, American Association for the Advancement of Science (published online Jun. 27, 2002).

Liu, Y., et al., "Transplants of Fibroblasts Genetically Modified to Express BDNF Promote Regeneration of Adult Rat Rubrospinal Axons and Recovery of Forelimb Function," *J. Neurosci.* 19:4370-4387, Society for Neuroscience with the assistance of Stanford University's HighWire Press™ (1999).

McKerracher, L., et al., "Identification of Myelin-Associated Glycoprotein as a Major Myelin-Derived Inhibitor of Neurite Growth," *Neuron* 13:805-811, Cell Press (1994).

Metz, G.A.S., et al., "Efficient testing of motor function in spinal cord injured rats," *Brain Res.* 883:165-177, Elsevier Science B.V. (2000).

Mikol, D.D. and Stefansson, K., "A Phosphatidylinositol-linked Peanut Agglutinin-binding Glycoprotein in Central Nervous System Myelin and on Oligodendrocytes," *J. Cell. Biol.* 106:1273-1279, The Rockefeller University Press (1988).

Mukhopadhyay, G., et al., "A Novel Role for Myelin-Associated Glycoprotein as an Inhibitor of Axonal Regeneration," *Neuron* 13:757-767, Cell Press (1994).

Noël, D., et al., "High In Vivo Production of a Model Monoclonal Antibody on Adenoviral Gene Transfer," *Human Gene Therapy* 13:1483-1493, Mary Ann Liebert, Inc. (Aug. 2002).

Ramon-Cueto, A., et al., "Functional Recovery of Paraplegic Rats and Motor Axon Regeneration in Their Spinal Cords by Olfactory Ensheathing Glia," *Neuron* 25:425-435, Cell Press (2000).

Rutishauser, U. and Jessell, T.M., "Cell Adhesion Molecules in Vertebrate Neural Development," *Physiol. Rev.* 68:819-857, the American Physiological Society (1988).

Wang, K.C., et al., "Oligodendrocyte-myelin glycoprotein is a Nogo receptor ligand that inhibits neurite outgrowth," *Nature* 417:941-944, Nature Publishing Group (Jun. 2002).

Wang, X., et al., "Localization of Nogo-A and Nogo-66 Receptor Proteins at Sites of Axon-Myelin and Synaptic Contact," *J. Neurosci.* 22:5505-5515, Society for Neuroscience with the assistance of Stanford University's HighWire Press™ (Jul. 2002).

Wang, H.-Y., et al., "Amyloid Peptide $A\beta_{1-42}$ Binds Selectively and with Picomolar Affinity to α7 Nicotinic Acetylcholine Receptors," *J. Neurochem.* 75:1155-1161, Lippincott Williams & Wilkins, Inc. (2000).

Weidner, N., et al., "Spontaneous corticospinal axonal platsicity and functional recovery after adult central nervous system injury," *Proc. Natl. Acad. Sci. USA* 98:3513-3518, The National Academy of Sciences (Mar. 2001).

Fournier, A.E., et al., "Characterization of the neuronal receptor mediating Nogo-66 inhibition of axonal regeneration," *J. Neurochem.* 78 (Suppl. 1):105, Blackwell Publishing, Abstract No.S08-01 (Sep. 2001).

Fournier, A.E., et al., "Nogo Receptor Domain Analysis," *Society for Neuroscience Abstracts* 27:670, Society for Neuroscience, Abstract No. 258.3, presented at the *Society for Neuroscience's 31st Annual Meeting*, San Diego, CA (Nov. 12, 2001).

GrandPre, T.J., et al., "Functional Analysis of Nogo-66 and Nogo Receptor Domains," *Society for Neuroscience Abstracts* 27:670, Society for Neuroscience, Abstract No. 258.4, presented at the *Society for Neuroscience's 31st Annual Meeting*, San Diego, CA (Nov. 12, 2001).

International Search Report for International Application No. PCT/US2005/002535, European Patent Office, Netherlands, mailed Oct. 24, 2005.

Li, M., et al., "Effect of soluble Nogo reeceptor treatment on functional and histological outcome after spinal cord injury in the rat," Biosis Database, Accession No. PREV200400194121, Abstract No. 80.22, *Presented at the 33rd Annual Meeting of the Society of Neuroscience*, New Orleans, LA (Nov. 8-12, 2003).

Li, W., et al., "A Neutralizing Anti-Nogo66 Receptor Monoclonal Antibody Reverses Inhibition of Neurite Outgrowth by Central Nervous System Myelin," *J. Biol. Chem.* 42:43780-43788, The American Society for Biochemistry and Molecular Biology, Inc. (Oct. 2004).

Li, W., et al., "Neutralization of NGR1 May Be Sufficient to Promote Rat DRG Neurite Outgrowth in the Presence of CNS Myeline," SFN 2003 Abstract Viewer & Itinerary Planner, Program No. 678.3, *Presented at the 33rd Annual Meeting of the Society of Neuroscience*, New Orleans, LA (Nov. 8-12, 2003).

Oertle, T., et al., "Nogo-A Inhibits Neurite Outgrowth and Cell Spreading with Three Discrete Regions," *J. Neurosci.* 23:5393-5406, Society for Neuroscience (Jul. 2003).

International Search Report for International Application No. PCT/US05/35719, mailed Apr. 13, 2006.

McGee, A. and Strittmatter, S., "The Nogo-66 receptor: focusing myelin inhibition of axon regeneration," *Trends Neurosci.* 26:193-198, Elsevier Applied Science Publishing (2003).

Supplementary Partial European Search Report for European Patent Application No. 04707073.5, European Patent Office, The Hague, mailed Sep. 5, 2006.

Supplementary Partial European Search Report for European Patent Application No. 03785123.5, European Patent Office, The Hague, mailed Oct. 5, 2006.

Grandpré, T. and Strittmatter, S.M., "Nogo: A Molecular Determinant of Axonal Growth and Regeneration," *The Neuroscientist* 7:5, 377-386, Sage Publications (2001).

International Search Report for Georgian Application No. AP 2001 008883, mailed on Mar. 22, 2007, National Centre of the Intellectual Property "Sakpatenti" of Georgia, Tbilisi.

Georgian Search Report for Georgian Application No. AP 2004 009281 completed on Aug. 29, 2007, National Centre of the Intellectual Property "Sakpatenti" of Georgia, Tbilisi, Georgia.

* cited by examiner

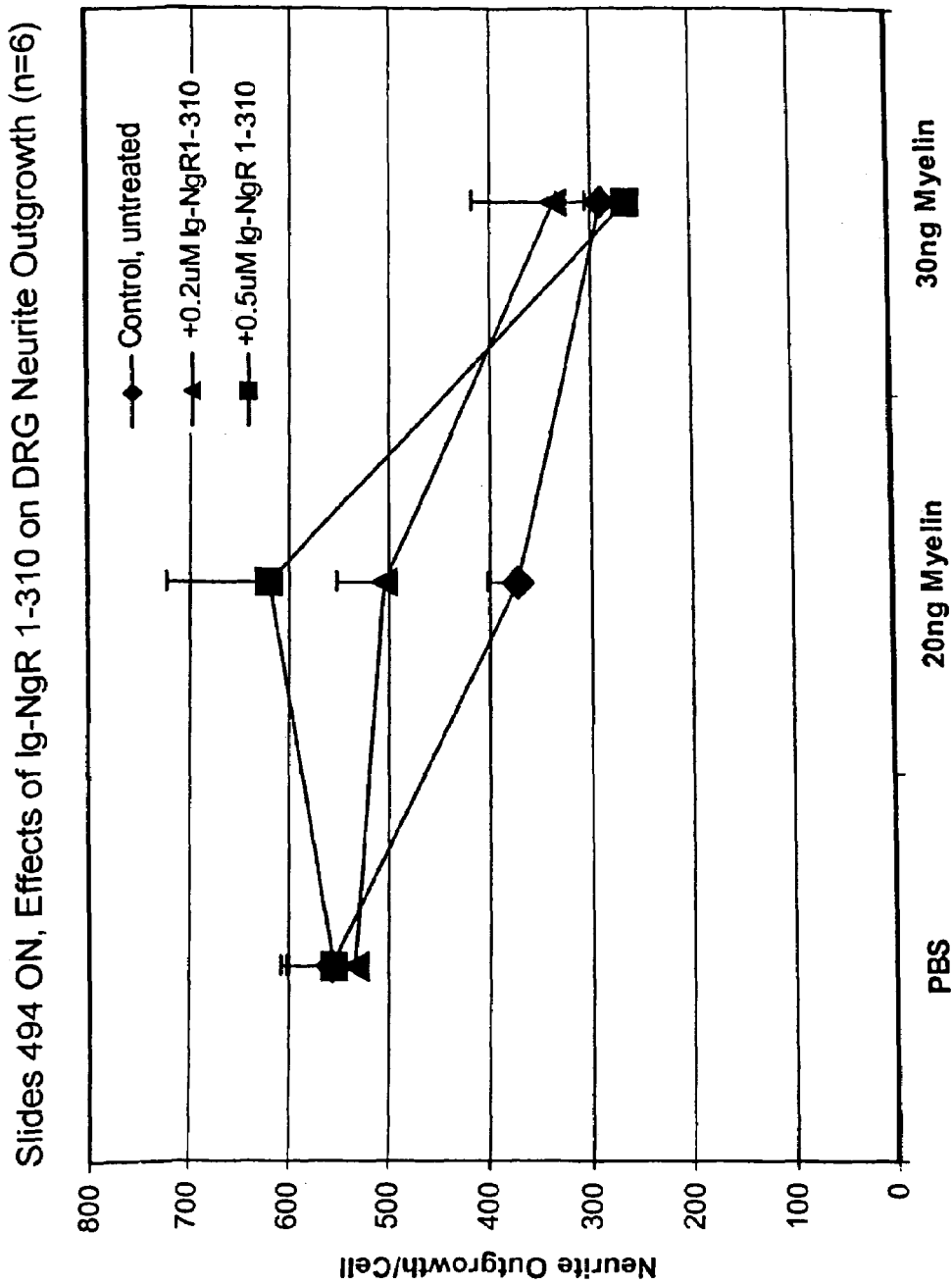

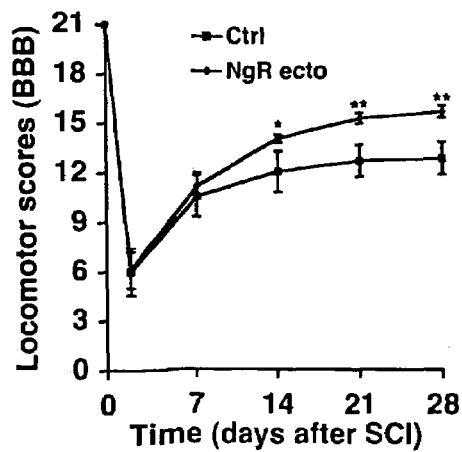
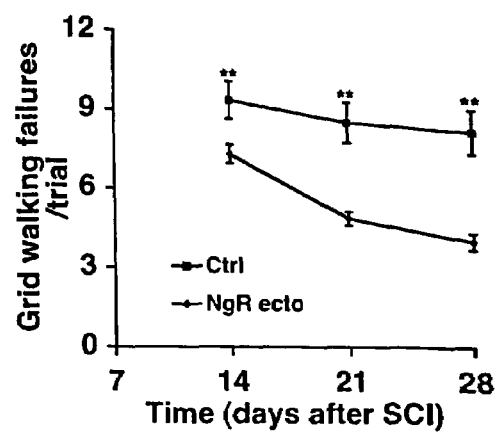
FIG. 14A  FIG. 14B
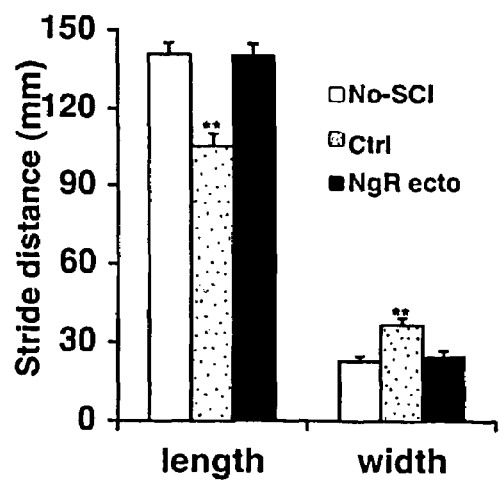
FIG. 14C

NOGO RECEPTOR ANTAGONISTS

This application is a continuation of International Application PCT/US03/25004, filed Aug. 7, 2003, which claims benefit from U.S. Provisional Application No. 60/402,866, filed Aug. 10, 2002, the disclosures of which are incorporated herein by reference in their entireties.

FIELD OF THE INVENTION

This invention relates to neurobiology and molecular biology. More particularly, this invention relates to immunogenic Nogo receptor-1 polypeptides, Nogo receptor-1 antibodies, antigen-binding fragments thereof, soluble Nogo receptors and fusion proteins thereof and nucleic acids encoding the same. This invention further relates to compositions comprising, and methods for making and using, such Nogo receptor antibodies, antigen-binding fragments thereof, immunogenic Nogo receptor-1 polypeptides, soluble Nogo receptors and fusion proteins thereof and nucleic acids encoding the same.

BACKGROUND OF THE INVENTION

Axons and dendrites of neurons are long cellular extensions from neurons. The distal tip of an extending axon or neurite comprises a specialized region, known as the growth cone. Growth cones sense the local environment and guide axonal growth toward the neuron's target cell. Growth cones respond to several environmental cues, for example, surface adhesiveness, growth factors, neurotransmitters and electric fields. The guidance of growth at the cone involves various classes of adhesion molecules, intercellular signals, as well as factors that stimulate and inhibit growth cones. The growth cone of a growing neurite advances at various rates, but typically at the speed of one to two millimeters per day.

Growth cones are hand shaped, with broad flat expansion (microspikes or filopodia) that differentially adhere to surfaces in the embryo. The filopodia are continually active, some filopodia retract back into the growth cone, while others continue to elongate through the substratum. The elongations between different filopodia form lamellipodia.

The growth cone explores the area that is ahead of it and on either side with its lamellipodia and filopodia. When an elongation contacts a surface that is unfavorable to growth, it withdraws. When an elongation contacts a favorable growth surface, it continues to extend and guides the growth cone in that direction. The growth cone can be guided by small variations in surface properties of the substrata. When the growth cone reaches an appropriate target cell a synaptic connection is created.

Nerve cell function is greatly influenced by the contact between the neuron and other cells in its immediate environment (U. Rutishauser, T. M. Jessell, Physiol. Rev. 1988, 68, p. 819). These cells include specialized glial cells, oligodendrocytes in the central nervous system (CNS), and Schwann cells in the peripheral nervous system (PNS), which ensheathe the neuronal axon with myelin (an insulating structure of multi-layered membranes) (G. Lemke, in An Introduction to Molecular Neurobiology, Z. Hall, Ed. [Sinauer, Sunderland, Mass., 1992], p. 281).

While CNS neurons have the capacity to regenerate after injury, they are inhibited from doing so because of the presence of inhibitory proteins present in myelin and possibly also by other types of molecules normally found in their local environment (Brittis and Flanagan, Neuron 2001, 30, pp. 11-14; Jones et al., J. Neurosci. 2002, 22, pp. 2792-2803; Grimpe et al., J. Neurosci. 2002, 22, pp. 3144-3160).

Several myelin inhibitory proteins that are found on oligodendrocytes have been characterized, e.g., NogoA (Chen et al., Nature, 2000, 403, 434-439; Grandpre et al., Nature 2000, 403, 439-444), myelin associated glycoprotein (MAG, McKerracher et al, Neuron 1994, 13, 805-811; Mukhopadhyay et al, Neuron 1994, 13, 757-767) and oligodendrocyte glycoprotein (OM-gp, Mikol and Stefansson, J. Cell. Biol. 1988, 106, 1273-1279). Each of these proteins has been separately shown to be a ligand for the neuronal Nogo receptor-1 (Wang et al., Nature 2002, 417, 941-944; Liu et al., Science, 2002, 297, 1190-93; Grandpre et al., Nature 2000, 403, 439-444; Chen et al., Nature, 2000, 403, 434-439; Domeniconi et al., Neuron, 2002, 35, 283-90).

Nogo receptor-1 is a GPI-anchored membrane protein that contains 8 leucine rich repeats (Fournier et al., Nature 2001, 409, 341-346). Upon interaction with an inhibitory protein (e.g., NogoA, MAG and OM-gp), the Nogo receptor-1 complex transduces signals that lead to growth cone collapse and inhibition of neurite outgrowth.

There is an urgent need for molecules that inhibit Nogo receptor-1 binding to its ligands and attenuate myelin-mediated growth cone collapse and inhibition of neurite outgrowth.

SUMMARY OF THE INVENTION

The invention relates to soluble Nogo receptor-1 polypeptides and fusion proteins comprising them, and antibodies and antigenic fragments thereof directed against specific immunogenic regions of Nogo receptor-1. The invention also relates to immunogenic Nogo receptor-1 polypeptides that bind to the antibodies of the invention. The invention further relates to nucleic acids encoding the polypeptides of this invention, vectors and host cells comprising such nucleic acids and methods of making the peptides. The antibodies, soluble receptors and receptor fusion proteins of this invention antagonize or block Nogo receptor-1 and are useful for inhibiting binding of Nogo receptor-1 to its ligands, inhibiting growth cone collapse in a neuron and decreasing the inhibition of neurite outgrowth or sprouting in a neuron.

In some embodiments, the invention provides an immunogenic polypeptide selected from the group consisting of SEQ ID NO: 1, SEQ ID NO: 2, SEQ ID NO: 3, SEQ ID NO: 4 and SEQ ID NO: 5.

In some embodiments, the invention provides nucleic acids encoding said immunogenic polypeptides, vectors comprising said nucleic acids and host cells comprising said nucleic acids or vectors. In some embodiments, the nucleic acid is operably linked to an expression control sequence.

In some embodiments, the invention provides a method of producing the immunogenic polypeptide comprising the steps of (a) culturing a host cell comprising the nucleic acid encoding an immunogenic peptide or the vector encoding the same; and (b) recovering the polypeptide from the host cell or culture medium.

In some embodiments, the invention provides a method of producing an antibody that specifically binds a Nogo receptor-1 comprising the steps of (a) immunizing a host with a polypeptide selected from the group consisting of SEQ ID NO: 1, SEQ ID NO: 2, SEQ ID NO: 3, SEQ ID NO: 4 and SEQ ID NO: 5 or a host cell expressing said polypeptides; and (b) recovering the antibody. In some embodiments, the antibody or antigen-binding fragment thereof is produced by this method. In some embodiments, the antibody or an antigen-binding fragment thereof specifically binds to a polypeptide selected from the group consisting of SEQ ID NO: 1, SEQ ID NO: 2, SEQ ID NO: 3, SEQ ID NO: 4 and SEQ ID NO: 5. In some embodiments, the antibody or antigen-binding fragment (a) inhibits growth cone collapse of a neuron; (b) decreases the inhibition of neurite outgrowth and sprouting in a neuron; and (c) inhibits Nogo receptor-1 binding to a ligand. In some embodiments, the antibody or antigen-binding fragment promotes survival of a neuron at risk of dying. In some embodiments, the neuron at risk of dying is in an animal, e.g., a mammal. In some embodiments, neurite outgrowth and sprouting is axonal growth. In some embodiments, the neuron is a central nervous system (CNS) neuron.

In some embodiments the antibody or antigen-binding fragment is a monoclonal antibody. In some embodiments, the antibody or antigen-binding fragment is a murine antibody. In some embodiments, the antibody is a humanized antibody, a chimeric antibody, or a single chain antibody.

In some embodiments, the invention provides a hybridoma cell line selected from the group consisting of HB 7E11 (ATCC® accession No. PTA-4587), HB 1H2 (ATCC® accession No. PTA-4584), HB 3G5 (ATCC® accession No. PTA-4586), HB 5B10 (ATCC® accession No. PTA-4588) and HB 2F7 (ATCC® accession No. PTA-4585). In some embodiments, the antibody or antigen-binding fragment thereof is produced by the hybridoma cell line.

In some embodiments the antibody or antigen-binding fragment thereof comprises a light chain comprising an amino acid sequence selected from the group consisting of (a) the amino acid sequence of SEQ ID NO: 15; (b) the amino acid sequence of SEQ ID NO: 16; and (c) an amino acid sequence comprising the CDR1, CDR2, and CDR3 amino acid sequences of SEQ ID NOs: 22, 23, and 24. In some embodiments the antibody or antigen-binding fragment thereof comprises a heavy chain comprising an amino acid sequence selected from the group consisting of (a) the amino acid sequence of SEQ ID NO: 17; (b) the amino acid sequence of SEQ ID NO: 18; and (c) an amino acid sequence comprising the CDR1, CDR2, and CDR3 amino acid sequences of SEQ ID NOs: 19, 20, and 21. In some embodiments, the invention provides a nucleic acid encoding said antibody or antigen-binding fragment thereof. In some embodiments, the nucleic acid is operably linked to an expression control sequence. In some embodiments, the invention provides a vector comprising said nucleic acid. In some embodiments, the invention provides a host cell comprising said nucleic acid or comprising a vector comprising the nucleic acid.

In some embodiments, the antibody or antigen-binding fragment thereof competitively inhibits the binding of an antibody produced by the hybridoma cell line to a Nogo receptor-1 or an immunogenic polypeptide selected from the group consisting of SEQ ID NO: 1, SEQ ID NO: 2, SEQ ID NO: 3, SEQ ID NO: 4 and SEQ ID NO: 5.

In some embodiments, the invention provides a method of inhibiting Nogo receptor-1 binding to a ligand, comprising the step of contacting Nogo receptor-1 with an antibody or antigen-binding fragment of this invention. In some embodiments, the ligand is selected from the group consisting of NogoA, NogoB, NogoC, MAG and OM-gp.

In some embodiments, the invention provides a method for inhibiting growth cone collapse in a neuron, comprising the step of contacting the neuron with the antibody or antigen-binding fragment thereof of this invention. In some embodiments, the invention provides a method for decreasing the inhibition of neurite outgrowth or sprouting in a neuron, comprising the step of contacting the neuron with the antibody or antigen-binding fragment of this invention. In some embodiments, the neuron is a CNS neuron. In some of these methods, the neurite outgrowth or sprouting is axonal growth.

In some embodiments the invention provides a method of promoting survival of a neuron at risk of dying, comprising contacting the neuron with an effective amount of (a) an anti-Nogo receptor-1 antibody or antigen-binding fragment thereof; or (b) a soluble Nogo receptor-1 polypeptide. In some embodiments, the soluble Nogo receptor-1 polypeptide is a fusion protein, e.g., an Fc-fusion protein. In some embodiments, the fusion protein is the sNogoR344-Fc protein. In some embodiments the neuron is in vitro. In some embodiments the neuron is in a mammal displaying signs or symptoms of, e.g., multiple sclerosis, ALS, Huntington's disease, Alzheimer's disease, Parkinson's disease, diabetic neuropathy, stroke, traumatic brain injuries and spinal cord injury.

In some embodiments, the invention provides a method of promoting survival of a neuron at risk of dying, the neuron being in a mammal, comprising (a) providing a cultured host cell expressing (i) an anti-Nogo receptor-1 antibody or antigen-binding fragment thereof; or (ii) a soluble Nogo receptor-1 polypeptide; and (b) introducing the host cell into the mammal at or near the site of the neuron.

In some embodiments, the invention provides a gene therapy method of promoting survival of a neuron in a mammal, which neuron is at risk of dying, comprising administering at or near the site of the neuron a viral vector comprising a nucleotide sequence that encodes (a) an anti-Nogo receptor-1 antibody or antigen-binding fragment; or (b) a soluble Nogo receptor-1 polypeptide, wherein the anti-Nogo receptor-1 antibody, antigen-binding fragment, or soluble Nogo receptor-1 polypeptide is expressed from the nucleotide sequence in the mammal in an amount sufficient to promote survival of the neuron.

In some embodiments, the invention provides a soluble Nogo receptor-1 polypeptide consisting essentially of a N-terminal domain (NT), 8 leucine rich repeat domains (LRR) and a LRR C-terminal domain (LRRCT) of Nogo receptor-1. In some embodiments, said soluble Nogo receptor-1 polypeptide is joined to a signal sequence. In some embodiments, the LRR comprises a heterologous LRR. In some embodiments, the invention provides a soluble Nogo receptor-1 polypeptide selected from the group consisting of: amino acid residues 26-344 of SEQ ID NO: 6; amino acid residues 26-310 of SEQ ID NO: 7; amino acid residues 26-344 of SEQ ID NO: 8; amino acid residues 26-310 of SEQ ID NO: 9; amino acid residues 27-344 of SEQ ID NO: 8; and amino acid residues 27-310 of SEQ ID NO: 9. In some embodiments, the invention provides a nucleic acid encoding said soluble Nogo receptor-1 polypeptide. In some embodiments, the nucleic acid is operably linked to an expression control sequence. In some embodiments, the invention provides a vector comprising said nucleic acid. In some embodiments, the invention provides a host cell comprising said nucleic acid or a vector comprising the nucleic acid.

In some embodiments, the invention provides a method of producing a soluble Nogo receptor-1 polypeptide of the invention comprising the steps of (a) culturing a host cell comprising a nucleic acid encoding the soluble Nogo receptor-1 polypeptide or a vector comprising the nucleic acid; and (b) recovering the polypeptide from the host cell or culture medium.

In some embodiments the invention provides a Nogo receptor-1 fusion protein comprising a soluble Nogo receptor-1 and a heterologous polypeptide. In some embodiments, the soluble Nogo receptor-1 polypeptide consists essentially of a N-terminal domain (NT), 8 leucine rich repeat domains (LRR) and a LRR C-terminal domain (LRRCT) of Nogo receptor-1. In some embodiments, the soluble Nogo receptor-1 polypeptide is joined to a signal sequence. In some embodiments, the Nogo receptor-1 fusion protein comprises a heterologous LRR. In some embodiments, the Nogo receptor-1 fusion protein comprises a polypeptide selected from the group consisting of: amino acid residues 26-344 of SEQ ID NO: 6; amino acid residues 26-310 of SEQ ID NO: 7; amino acid residues 26-344 of SEQ ID NO: 8; amino acid residues 26-310 of SEQ ID NO: 9; amino acid residues 27-344 of SEQ ID NO: 8; and amino acid residues 27-310 of SEQ ID NO: 9. In some embodiments the heterologous polypeptide comprises an immunoglobulin constant region. In some embodiments, the immunoglobulin constant region is an immunoglobulin heavy chain constant region. In some embodiments, the immunoglobulin heavy chain constant region is an IgG heavy chain constant region. In some embodiments, the heterologous polypeptide is an Fc region. In some embodiments, the Nogo receptor-1 fusion protein is a dimer.

In some embodiments, the invention provides a nucleic acid encoding the Nogo receptor-1 fusion protein. In some embodiments, the nucleic acid encoding the Nogo receptor-1 fusion protein is operably linked to an expression control sequence.

In some embodiments, the invention provides a vector comprising the nucleic acid encoding the Nogo receptor-1 fusion protein.

In some embodiments, the invention provides a host cell comprising the nucleic acid encoding the Nogo receptor-1 fusion protein or the vector comprising the nucleic acid encoding the Nogo receptor-1 fusion protein.

In some embodiments, the invention provides a method of producing the Nogo receptor-1 fusion protein comprising the steps of (a) culturing a host cell comprising a nucleic acid encoding the Nogo receptor-1 fusion protein or a vector comprising the nucleic acid; and (b) recovering the Nogo receptor-1 fusion protein from the host cell or culture medium.

In some embodiments, the invention provides a method of inhibiting Nogo receptor-1 binding to a ligand, comprising the step of contacting the ligand with the soluble Nogo receptor-1 polypeptide or the Nogo receptor-1 fusion protein of this invention.

In some embodiments, the invention provides a method of modulating an activity of a Nogo receptor-1 ligand, comprising the step of contacting the Nogo receptor-1 ligand with a soluble Nogo receptor-1 polypeptide or a Nogo receptor-1 fusion protein of the invention.

In some embodiments, the invention provides a method for inhibiting growth cone collapse in a neuron, comprising the step of contacting a Nogo receptor-1 ligand with a soluble Nogo receptor-1 polypeptide or a Nogo receptor-1 fusion protein of this invention. In some embodiments, the invention provides a method for decreasing the inhibition of neurite outgrowth or sprouting in a neuron, comprising the step of contacting a Nogo receptor-1 ligand with the soluble Nogo receptor-1 polypeptide or the Nogo receptor-1 fusion protein of this invention. In some embodiments, the neuron is a CNS neuron. In some embodiments, the ligand is selected from the group consisting of NogoA, NogoB, NogoC, MAG and OM-gp. In some embodiments, the neurite outgrowth or sprouting is axonal growth.

In some embodiments, the invention provides a composition comprising a pharmaceutically acceptable carrier and a component selected from (a) an antibody or an antigen-binding fragment according to this invention; (b) a soluble Nogo receptor-1 polypeptide according to this invention; and (c) a Nogo receptor-1 fusion protein according to this invention. In some embodiments, the composition further comprises one or more additional therapeutic agents.

BRIEF DESCRIPTION OF THE DRAWINGS

FIG. 10A is a graph depicting the effect of sNogoR310-Fc on P4 rat DRG neurite outgrowth in the presence or absence of increasing amounts of myelin.

FIG. 14A shows the locomotor BBB score as a function of time after dorsal hemisection in vehicle or sNogoR310-Fc treated animals. FIG. 14B shows hindlimb errors during grid walking as a function of time after injury. FIG. 14C shows footprint analysis revealing a shorter stride length and a greater stride width in control mice than uninjured or injured+ sNogoR310-Fc rats. In all the graphs, means±s.e.m. from 7-9 rats in each group are reported. The values of sNogoR310-Fc group are statistically different from the control (FIGS. 14A-B). The control values are statistically different from no-SCI or SCI+sNogoR310-Fc rats in FIG. 14C. (asterisk, p<0.05; double asterisks, p<0.01; Student's t-test).

DETAILED DESCRIPTION OF THE INVENTION

Definitions and General Techniques

Figure 1:
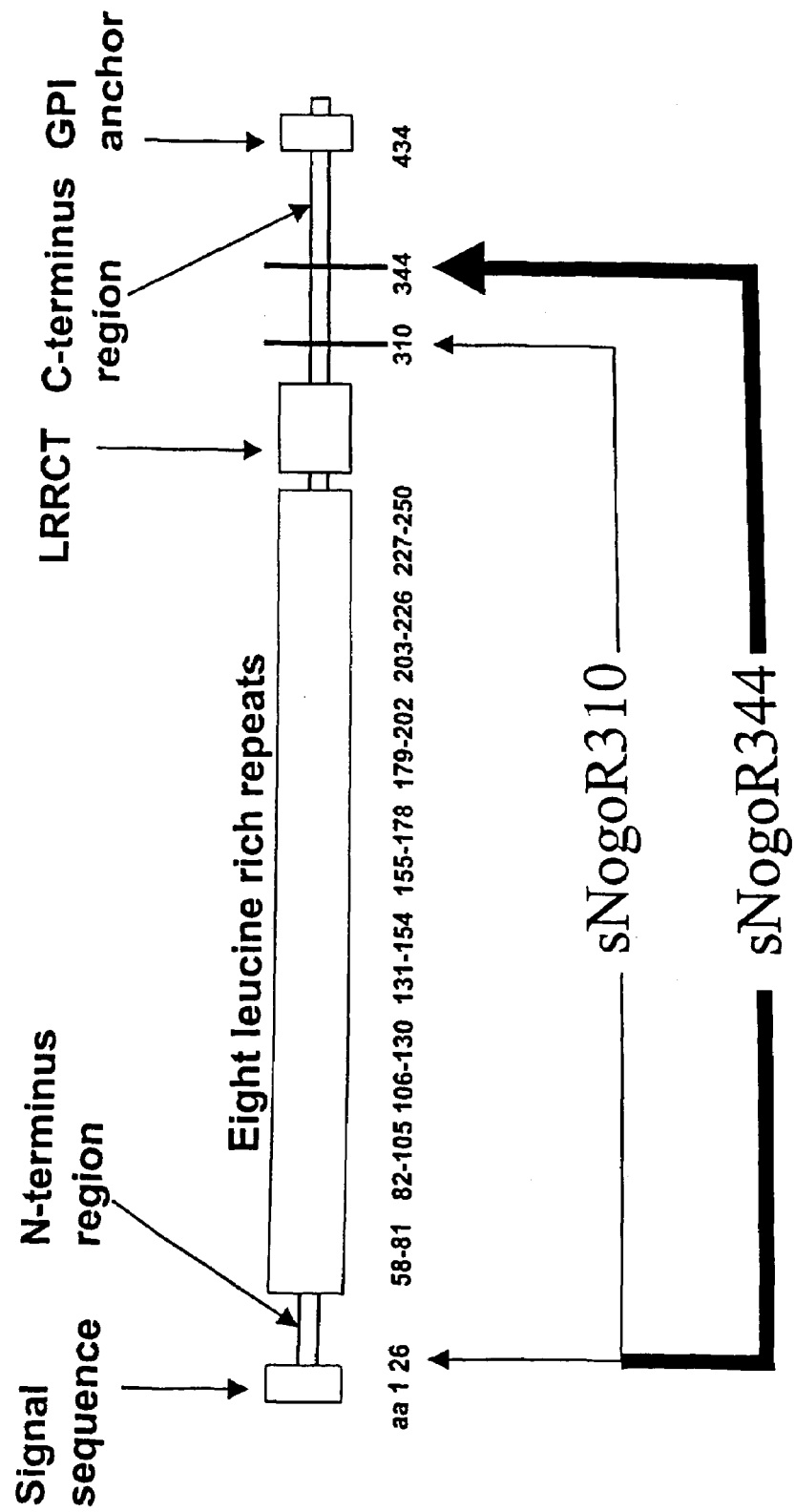
FIG. 1 is a schematic representation of the structure of Nogo receptor-1. Human sNogoR310 contains residues 26-310 and sNogoR344 contains residues 26-344. Rat sNogoR310 contains residues 27-310 and sNogoR344 contains residues 27-344

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

Although methods and materials similar or equivalent to those described herein can be used in practice or testing of the present invention, suitable methods and materials are described below. The materials, methods and examples are illustrative only, and are not intended to be limiting. Other features and advantages of the invention will be apparent from the detailed description and from the claims.

Throughout this specification and claims, the word "comprise," or variations such as "comprises" or "comprising," will be understood to imply the inclusion of a stated integer or group of integers but not the exclusion of any other integer or group of integers.

In order to further define this invention, the following terms and definitions are herein provided.

As used herein, "antibody" means an intact immunoglobulin, or an antigen-binding fragment thereof. Antibodies of this invention can be of any isotype or class (e.g., M, D, G, E and A) or any subclass (e.g., G1-4, A1-2) and can have either a kappa (κ) or lambda (λ) light chain.

As used herein, "Fc" means a portion of the heavy chain constant region of an antibody that is obtainable by papain digestion.

As used herein, "NogoR fusion protein" means a protein comprising a soluble Nogo receptor-1 moiety fused to a heterologous polypeptide.

As used herein, "humanized antibody" means an antibody in which at least a portion of the non-human sequences are replaced with human sequences. Examples of how to make humanized antibodies may be found in U.S. Pat. Nos. 6,054,297, 5,886,152 and 5,877,293.

As used herein, "chimeric antibody" means an antibody that contains one or more regions from a first antibody and one or more regions from at least one other antibody. The first antibody and the additional antibodies can be from the same or different species.

As used herein and in U.S. patent application 60/402,866, "Nogo receptor," "NogoR," "NogoR-1," "NgR," and "NgR-1" each means Nogo receptor-1.

Immunogenic Nogo Receptor-1 Polypeptides

In one aspect the present invention relates to Nogo receptor-1 polypeptides that are immunogenic. In some embodiments of the invention, the immunogenic polypeptide consists essentially of an amino acid sequence selected from the group consisting of: LDLSDNAQLRVVDPTT (rat)(SEQ ID NO: 1); LDLSDNAQLRSVDPAT (human)(SEQ ID NO: 2); AVASGPFRPFQTNQLTDEELLGLPKCCQPDAADKA (rat)(SEQ ID NO: 3); AVATGPYHPIWTGRATDEEPLGLP-KCCQPDAADKA (human)(SEQ ID NO: 4); and CRLGQAGSGA (mouse) (SEQ ID NO: 5).

In some embodiments, the invention relates to a nucleic acid encoding a polypeptide of SEQ ID NOs: 1-5. In some embodiments of the invention, the nucleic acid molecule is linked to an expression control sequence (e.g., pcDNA(I)).

The present invention also relates to a vector comprising a nucleic acid coding for an immunogenic polypeptide of the invention. In some embodiments of the invention, the vector is a cloning vector. In some embodiments of the invention, the vector is an expression vector. In some embodiments of the invention, the vector contains at least one selectable marker.

The present invention also relates to host cells comprising the above-described nucleic acid or vector.

The present invention also relates to a method of producing an immunogenic polypeptide of the invention comprising the step of culturing a host cell. In some embodiments, the host cell is prokaryotic. In some embodiments, the host cell is eukaryotic. In some embodiments, the host cell is yeast.

Antibodies

The present invention further relates to an antibody or an antigen-binding fragment thereof that specifically binds an immunogenic Nogo receptor-1 polypeptide of the invention. In some embodiments the antibody or antigen-binding fragment binds a polypeptide consisting essentially of an amino acid sequence selected from the group consisting of SEQ ID NOs: 1-5. The antibody or antigen-binding fragment of the present invention may be produced in vivo or in vitro. Production of the antibody or antigen-binding fragment is discussed below.

An antibody or an antigen-binding fragment thereof of the invention inhibits the binding of Nogo receptor-1 to a ligand (e.g., NogoA, NogoB, NogoC, MAG, OM-gp) and decreases myelin-mediated inhibition of neurite outgrowth and sprouting, particularly axonal growth, and attenuates myelin mediated growth cone collapse.

In some embodiments, the anti-Nogo receptor-1 antibody or antigen-binding fragment thereof is murine. In some embodiments, the Nogo receptor-1 is from rat. In other embodiments, the Nogo receptor-1 is human. In some embodiments the anti-Nogo receptor-1 antibody or antigen-binding fragment thereof is recombinant, engineered, humanized and/or chimeric.

In some embodiments, the antibody is selected from the group consisting of: monoclonal 7E11 (ATCC® accession No. PTA-4587); monoclonal 1H2 (ATCC® accession No. PTA-4584); monoclonal 2F7 (ATCC® accession No. PTA-4585); monoclonal 3G5 (ATCC® accession No. PTA-4586); and monoclonal 5B10 (ATCC® accession No. PTA-4588). In some embodiments, the antibody is polyclonal antibody 46.

Exemplary antigen-binding fragments are, Fab, Fab', F(ab')$_2$, Fv, Fd, dAb, and fragments containing complementarity determining region (CDR) fragments, single-chain antibodies (scFv), chimeric antibodies, diabodies and polypeptides that contain at least a portion of an immunoglobulin that is sufficient to confer specific antigen-binding to the polypeptide (e.g., immunoadhesins).

As used herein, Fd means a fragment that consists of the $V_H$ and $C_{H1}$ domains; Fv means a fragment that consists of the $V_L$ and $V_H$ domains of a single arm of an antibody; and dAb means a fragment that consists of a $V_H$ domain (Ward et al., Nature 341:544-546, 1989). As used herein, single-chain antibody (scFv) means an antibody in which a $V_L$ region and a $V_H$ region are paired to form a monovalent molecules via a synthetic linker that enables them to be made as a single protein chain (Bird et al., Science 242:423-426, 1988 and Huston et al., Proc. Natl. Acad. Sci. USA 85:5879-5883, 1988). As used herein, diabody means a bispecific antibody in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al., Proc. Natl. Acad. Sci. USA 90:6444-6448, 1993, and Poljak, R. J., et al., Structure 2:1121-1123, 1994). As used herein, immunoadhesin that specifically binds an antigen of interest, means a molecule in which one or more CDRs may be incorporated, either covalently or noncovalently.

In some embodiments, the invention provides a subunit polypeptide of a Nogo receptor-1 antibody of the invention, wherein the subunit polypeptide is selected from the group consisting of: (a) a heavy chain or a variable region thereof; and (b) a light chain or a variable region thereof.

In some embodiments, the invention provides a nucleic acid encoding the heavy chain or the variable region thereof, or the light chain and the variable region thereof of a subunit polypeptide of a Nogo receptor-1 antibody of the invention.

In some embodiments, the invention provides a hypervariable region (CDR) of a Nogo receptor-1 antibody of the invention or a nucleic acid encoding a CDR.

Immunization

Antibodies of the invention can be generated by immunization of a suitable host (e.g., vertebrates, including humans, mice, rats, sheep, goats, pigs, cattle, horses, reptiles, fishes, amphibians, and in eggs of birds, reptiles and fish). Such antibodies may be polyclonal or monoclonal.

In some embodiments, the host is immunized with an immunogenic Nogo receptor-1 polypeptide of the invention. In other embodiments, the host is immunized with Nogo receptor-1 associated with the cell membrane of an intact or disrupted cell and antibodies of the invention are identified by binding to an immunogenic Nogo receptor-1 polypeptide of the invention.

In some embodiments, the Nogo receptor-1 antigen is administered with an adjuvant to stimulate the immune response. Adjuvants often need to be administered in addition to antigen in order to elicit an immune response to the antigen. These adjuvants are usually insoluble or undegradable substances that promote nonspecific inflammation, with recruitment of mononuclear phagocytes at the site of immunization. Examples of adjuvants include, but are not limited to, Freund's adjuvant, RIBI (muramyl dipeptides), ISCOM (immunostimulating complexes) or fragments thereof.

For a review of methods for making antibodies, see e.g., Harlow and Lane (1988), *Antibodies, A Laboratory Manual*, Yelton, D. E. et al. (1981); Ann. Rev. of Biochem., 50, pp. 657-80., and Ausubel et al. (1989); Current Protocols in Molecular Biology (New York: John Wiley & Sons). Determination of immunoreactivity with an immunogenic Nogo receptor-1 polypeptide of the invention may be made by any of several methods well known in the art, including, e.g., immunoblot assay and ELISA.

Production of Antibodies and Antibody Producing Cell Lines

Monoclonal antibodies of the invention can made by standard procedures as described, e.g., in Harlow and Lane (1988), supra.

Briefly, at an appropriate period of time the animal is sacrificed and lymph node and/or splenic B-cells are immortalized by any one of several techniques that are well-known in the art, including but not limited to transformation, such as with EBV or fusion with an immortalized cell line, such as myeloma cells. Thereafter, the cells are clonally separated and the supernatants of each clone tested for production of an antibody specific for an immunogenic Nogo receptor-1 polypeptide of the invention. Methods of selecting, cloning and expanding hybridomas are well known in the art. Similarly, methods for identifying the nucleotide and amino acid sequence of the immunoglobulin genes are known in the art.

Other suitable techniques for producing an antibody of the invention involve in vitro exposure of lymphocytes to the Nogo receptor-1 or to an immunogenic polypeptide of the invention, or alternatively, selection of libraries of antibodies in phage or similar vectors. See Huse et al., Science, 246, pp. 1275-81 (1989). Antibodies useful in the present invention may be employed with or without modification.

Antigens (in this case Nogo receptor-1 or an immunogenic polypeptide of the invention) and antibodies can be labeled by joining, either covalently or non-covalently, a substance that provides for a detectable signal. Various labels and conjugation techniques are known in the art and can be employed in practicing the invention. Suitable labels include, but are not limited to, radionucleotides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

In some embodiments of the invention, an antibody has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth (see below for more detailed discussion).

The antibodies of this invention may also be human monoclonal antibodies, for example those produced by immortalized human cells, by SCID-hu mice or other non-human animals capable of producing "human" antibodies.

Phage Display Libraries

Anti-Nogo receptor-1 antibodies of this invention can be isolated by screening a recombinant combinatorial antibody library. Exemplary combinatorial libraries are for binding to an immunogenic Nogo receptor-1 polypeptide of the invention, such as a scFv phage display library, prepared using $V_L$ and $V_H$ cDNAs prepared from mRNA derived an animal immunized with an immunogenic Nogo receptor-1 polypeptide of the invention. Methodologies for preparing and screening such libraries are known in the art. There are commercially available methods and materials for generating phage display libraries (e.g., the Pharmacia Recombinant Phage Antibody System, catalog no. 27-9400-01; the Stratagene SurfZAP™ phage display kit, catalog no. 240612; and others from MorphoSys). There are also other methods and reagents that can be used in generating and screening antibody display libraries (see e.g., Ladner et al. U.S. Pat. No.

5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nucl. Acids Res. 19:4133-4137; and Barbas et al. (1991) Proc. Natl. Acad. Sci. USA 88:7978-7982.

Following screening and isolation of an anti-Nogo receptor-1 antibody of the invention from a recombinant immunoglobulin display library, the nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express an antibody isolated by screening a combinatorial library, DNA encoding the antibody heavy chain and light chain or the variable regions thereof is cloned into a recombinant expression vector and introduced into a mammalian host cell, as described above.

Class Switching

Anti-Nogo receptor-1 antibodies of the invention can be of any isotype. An antibody of any desired isotype can be produced by class switching. For class switching, nucleic acids encoding $V_L$ or $V_H$, that do not include any nucleotide sequences encoding $C_L$ or $C_H$, are isolated using methods well known in the art. The nucleic acids encoding $V_L$ or $V_H$ are then operatively linked to a nucleotide sequence encoding a $C_L$ or $C_H$ from a desired class of immunoglobulin molecule. This may be achieved using a vector or nucleic acid that comprises a $C_L$ or $C_H$ chain, as described above. For example, an anti-Nogo receptor-1 antibody of the invention that was originally IgM may be class switched to an IgG. Further, the class switching may be used to convert one IgG subclass to another, e.g., from IgG1 to IgG2.

Mutated Antibodies

In other embodiments, antibodies or antigen-binding fragments of the invention may be mutated in the variable domains of the heavy and/or light chains to alter a binding property of the antibody. For example, a mutation may be made in one or more of the CDR regions to increase or decrease the $K_d$ of the antibody for Nogo receptor-1, to increase or decrease $K_{off}$, or to alter the binding specificity of the antibody. Techniques in site-directed mutagenesis are well known in the art. See e.g., Sambrook et al. and Ausubel et al., supra. In a preferred embodiment, mutations are made at an amino acid residue that is known to be changed compared to germline in a variable region of an anti-Nogo receptor-1 antibody of the invention. In some embodiments, mutations are made at one or more amino acid residues that are known to be changed compared to the germline in a variable region of an anti-Nogo receptor-1 antibody of the invention. In another embodiment, a nucleic acid encoding an antibody heavy chain or light chain variable region is mutated in one or more of the framework regions. A mutation may be made in a framework region or constant domain to increase the half-life. A mutation in a framework region or constant domain also may be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

Fusion Antibodies and Immunoadhesins

In another embodiment, a fusion antibody or immunoadhesin may be made which comprises all or a portion of an anti-Nogo receptor-1 antibody of the invention linked to another polypeptide. In some embodiments, only the variable region of the anti-Nogo receptor-1 antibody is linked to the polypeptide. In other embodiments, the $V_H$ domain of an anti-Nogo receptor-1 antibody of this invention is linked to a first polypeptide, while the $V_L$ domain of the antibody is linked to a second polypeptide that associates with the first polypeptide in a manner that permits the $V_H$ and $V_L$ domains to interact with one another to form an antibody binding site. In other embodiments, the $V_H$ domain is separated from the $V_L$ domain by a linker that permits the $V_H$ and $V_L$ domains to interact with one another (see below under Single Chain Antibodies). The $V_H$-linker-$V_L$ antibody is then linked to a polypeptide of interest. The fusion antibody is useful to directing a polypeptide to a cell or tissue that expresses a Nogo receptor-1 ligand. The polypeptide of interest may be a therapeutic agent, such as a toxin, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

Single Chain Antibodies

The present invention includes a single chain antibody (scFv) that binds an immunogenic Nogo receptor-1 polypeptide of the invention. To produce the ScFv, $V_H$- and $V_L$-encoding DNA is operatively linked to DNA encoding a flexible linker, e.g., encoding the amino acid sequence (Gly$_4$-Ser)$_3$ (SEQ ID NO: 10), such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554). The single chain antibody may be monovalent, if only a single $V_H$ and $V_L$ are used, bivalent, if two $V_H$ and $V_L$ are used, or polyvalent, if more than two $V_H$ and VL are used.

Chimeric Antibodies

The present invention further includes a bispecific antibody or antigen-binding fragment thereof in which one specificity is for an immunogenic Nogo receptor-1 polypeptide of the invention. In one embodiment, a chimeric antibody can be generated that specifically binds to an immunogenic Nogo receptor-1 polypeptide of the invention through one binding domain and to a second molecule through a second binding domain. The chimeric antibody can be produced through recombinant molecular biological techniques, or may be physically conjugated together. In addition, a single chain antibody containing more than one $V_H$ and $V_L$ may be generated that binds specifically to an immunogenic polypeptide of the invention and to another molecule that is associated with attenuating myelin mediated growth cone collapse and inhibition of neurite outgrowth and sprouting. Such bispecific antibodies can be generated using techniques that are well known for example, Fanger et al. *Immunol Methods* 4: 72-81 (1994) and Wright and Harris, supra. and in connection with (iii) see e.g., Traunecker et al. *Int. J. Cancer* (Suppl.) 7: 51-52 (1992).

In some embodiments, the chimeric antibodies are prepared using one or more of the variable regions from an antibody of the invention. In another embodiment, the chimeric antibody is prepared using one or more CDR regions from said antibody.

Derivatized and Labeled Antibodies

An antibody or an antigen-binding fragment of the invention can be derivatized or linked to another molecule (e.g., another peptide or protein). In general, the antibody or antigen-binding fragment is derivatized such that binding to an immunogenic polypeptide of the invention is not affected adversely by the derivatization or labeling. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antigen-binding fragment with another molecule (such as a streptavidin core region or a polyhistidine tag).

In some embodiments, a derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

In some embodiments, the derivatized antibody is a labeled antibody. Exemplary, detection agents with which an antibody or antibody portion of the invention may be derivatized are fluorescent compounds, including fluorescein, fluorescein isothiocyanate, rhodamine, 5-dimethylamine-1-napthalenesulfonyl chloride, phycoerythrin, lanthanide phosphors and the like. An antibody also may be labeled with enzymes that are useful for detection, such as horseradish peroxidase, β-galactosidase, luciferase, alkaline phosphatase, glucose oxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitopes recognized by a secondary reporter (e.g., leucine zipper pair sequences, binding sites for secondary antibodies, metal binding domains, epitope tags).

An anti-Nogo receptor-1 antibody or an antigen-fragment thereof also may be labeled with a radio-labeled amino acid. The radiolabel may be used for both diagnostic and therapeutic purposes. The radio-labeled anti-Nogo receptor-1 antibody may be used diagnostically, for example, for determining Nogo receptor-1 levels in a subject. Further, the radio-labeled anti-Nogo receptor-1 antibody may be used therapeutically for treating spinal cord injury. Examples of labels for polypeptides include, but are not limited to, the following radioisotopes or radionucleotides —$^{3}H$, $^{14}C$, $^{15}N$, $^{35}S$, $^{90}Y$, $^{99}Tc$, $^{111}In$, $^{125}I$, $^{131}I$.

An anti-Nogo receptor-1 antibody or an antigen-fragment thereof may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

Characterization of Anti-Nogo receptor-1 Antibodies

Class and Subclass of Anti-Nogo receptor-1 Antibodies

The class and subclass of anti-Nogo receptor-1 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

Binding Affinity of Anti-Nogo Receptor-1 Antibody to Nogo Receptor-1

The binding affinity and dissociation rate of an anti-Nogo receptor-1 antibody of the invention to an immunogenic Nogo receptor-1 polypeptide of the invention may be determined by any method known in the art. For example, the binding affinity can be measured by competitive ELISAs, RIAs, BIAcore or KinExA technology. The dissociation rate also can be measured by BIAcore or KinExA technology. The binding affinity and dissociation rate are measured by surface plasmon resonance using, e.g., a BIAcore.

The $K_d$ of 7E11 and 1H2 were determined to be $1 \times 10^{-7}$ M and $2 \times 10^{-8}$ M, respectively.

Inhibition of Nogo Receptor-1 Activity by Anti-Nogo Receptor-1 Antibody

In some embodiments, an anti-Nogo receptor-1 antibody or an antigen-binding fragment of the invention thereof inhibits the binding of Nogo receptor-1 to a ligand. The $IC_{50}$ of such inhibition can be measured by any method known in the art, e.g., by ELISA, RIA, or Functional Antagonism. In some embodiments, the $IC_{50}$ is between 0.1 and 500 nM. In some embodiments, the $IC_{50}$ is between 10 and 400 nM. In yet other embodiments, the antibody or portion thereof has an $IC_{50}$ of between 60 nM and 400 nM. The $IC_{50}$ of 7E11 and 1H2 were determined to be 400 nM and 60 nM, respectively, in a binding assay. See also Table 3, infra.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Compositions comprising, and uses of, the antibodies of the present invention are described below.

Soluble Nogo Receptor-1 Polypeptides

Protein

Full-length Nogo receptor-1 consists of a signal sequence, a N-terminus region (NT), eight leucine rich repeats (LRR), a LRRCT region (a leucine rich repeat domain C-terminal of the eight leucine rich repeats), a C-terminus region (CT) and a GPI anchor (see FIG. 1).

Some embodiments of the invention provide a soluble Nogo receptor-1 polypeptide. Soluble Nogo receptor-1 polypeptides of the invention comprise an NT domain; 8 LRRs and an LRRCT domain and lack a signal sequence and a functional GPI anchor (i.e., no GPI anchor or a GPI anchor that lacks the ability to efficiently associate to a cell membrane).

In some embodiments, a soluble Nogo receptor-1 polypeptide comprises a heterologous LRR. In some embodiments a soluble Nogo receptor-1 polypeptide comprises 2, 3, 4, 5, 6, 7, or 8 heterologous LRR's. A heterologous LRR means an LRR obtained from a protein other than Nogo receptor-1. Exemplary proteins from which a heterologous LRR can be obtained are toll-like receptor (TLR1.2); T-cell activation leucine repeat rich protein; deceorin; OM-gp; insulin-like growth factor binding protein acidic labile subunit slit and robo; and toll-like receptor 4.

In some embodiments, the invention provides a soluble Nogo receptor-1 polypeptide of 319 amino acids (soluble Nogo receptor-1 344, sNogoR1-344, or sNogoR344) (residues 26-344 of SEQ ID NOs: 6 and 8 or residues 27-344 of SEQ ID NO: 8). In some embodiments, the invention provides a soluble Nogo receptor-1 polypeptide of 285 amino acids (soluble Nogo receptor-1 310, sNogoR1-310, or sNogoR310) (residues 26-310 of SEQ ID NOs: 7 and 9 or residues 27-310 of SEQ ID NO: 9). See FIG. 1.

TABLE 1

Sequences of Human and Rat
Nogo receptor-1 Polypeptides

SEQ ID NO: 6 MKRASAGGSRLLAWVLWLQAWQVAAPCPGACVCYNEP
(human 1-344) KVTTSCPQQGLQAVPVGIPAASQRIFLHGNRISHVPA
ASFRACRNLTILWLHSNVLARIDAAAFTGLALLEQLD
LSDNAQLRSVDPATFHGLGRLHTLHLDRCGLQELGPG
LFRGLAALQYLYLQDNALQALPDDTFRDLGNLTHLFL
HGNRISSVPERAFRGLHSLDRLLLHQNRVAHVHPHAF
RDLGRLMTLYLFANNLSALPTEALAPLRALQYLRLND
NPWVCDCRARPLWAWLQKFRGSSSEVPCSLPQRLAGR
DLKRLAANDLQGCAVATGPYHPIWTGRATDEEPLGLP
KCCQPDAADKA SEQ ID NO: 7 MKRASAGGSRLLAWVLWLQAWQVAAPCPGACVCYNEP
(human 1-310) KVTTSCPQQGLQAVPVGIPAASGRIFLHGNRISHVPA
ASFRACRNLTILWLHSNVLARIDAAAFTGLALLEQLD
LSDNAQLRSVDPATFHGLGRLHTLHLDRCGLQELGPG
LFRGLAALQYLYLQDNALQALPDDTFRDLGNLTHLFL
HGNRISSVPERAFRGLHSLDRLLLHQNRVAHVHPHAF
RDLGRLMTLYLFANNLSALPTEALAPLRALQYLRLND
NPWVCDCRARPLWAWLQKFRGSSSEVPCSLPQRLAGR
DLKRLAANDLQGCA SEQ ID NO: 8 MKRASSGGSRLPTWVLWLQAWRVATPCPGACVCYNEP
(rat 1-344) KVTTSRPQQGLQAVPAGIPASSQRIFLHGNRISYVPA
ASFQSCRNLTILWLHSNALAGIDAAAFTGLTLLEQLD
LSDNAQLRVVDPTTFRGLGHLHTLHLDRCGLQELGPG
LFRGLAALQYLYLQDNNLQALPDNTFRDLGNLTHLFL
HGNRIPSVPEHAFRGLHSLDRLLLHQNHVARVHPHAF
RDLGRLMTLYLFANNLSMLPAEVLVPLRSLQYLRLND
NPWVCDCRARPLWAWLQKFRGSSSGVPSNLPQRLAGR
DLKRLATSDLEGCAVASGPFRPFQTNQLTDEELLGLP
KCCQPDAADKA SEQ ID NO: 9 MKRASSGGSRLPTWVLWLQAWRVATPCPGACVCYNEP
(rat 1-310) KVTTSRPQQGLQAVPAGIPASSQRIFLHGNRISYVPA
ASFQSCRNLTILWLHSNALAGIDAAAFTGLTLLEQLD
LSDNAQLRVVDPTTFRGLGHLHTLHLDRCGLQELGPG
LFRGLAALQYLYLQDNNLQALPDNTFRDLGNLTHLFL
HGNRIPSVPEHAFRGLHSLDRLLLHQNHVARVHPHAF
RDLGRLMTLYLFANNLSMLPAEVLVPLRSLQYLRLND
NPWVCDCRARPLWAWLQKFRGSSSGVPSNLPQRLAGR
DLKRLATSDLEGCA In some embodiments of the invention, the soluble Nogo receptor-1 polypeptides of the invention are used to inhibit the binding of a ligand to Nogo receptor-1 and act as an antagonist of Nogo receptor-1 ligands. In some embodiments of the invention, the soluble Nogo receptor-1 polypeptides of the invention are used to decrease inhibition of neurite outgrowth and sprouting in a neuron, such as axonal growth and to inhibit myelin mediated growth cone collapse in a neuron. In some embodiments, the neuron is a CNS neuron.

sNogoR310 and sNogoR344, surprisingly, block the binding of NogoA, NogoB, NogoC, MAG and OM-gp to Nogo receptor-1.

In some embodiments, the soluble Nogo receptor-1 polypeptide of the invention is a component of a fusion protein that further comprises a heterologous polypeptide. In some embodiments, the heterologous polypeptide is an immunoglobulin constant domain. In some embodiments, the immunoglobulin constant domain is a heavy chain constant domain. In some embodiments, the heterologous polypeptide is an Fc fragment. In some embodiments the Fc is joined to the C-terminal end of the soluble Nogo receptor-1 polypeptide of the invention. In some embodiments the fusion Nogo receptor-1 protein is a dimer.

Nucleic Acid Molecules of the Present Invention

The present invention provide a nucleic acid that encodes a polypeptide of the invention, including the polypeptides of any one of SEQ ID NOs: 1-9. In some embodiments, the nucleic acid encodes a polypeptide selected from the group consisting of amino acid residues 26-344 of Nogo receptor-1 as shown in SEQ ID NOs: 6 and 8 or amino acid residues 27-344 of Nogo receptor-1 as shown in SEQ ID NO: 8. In some embodiments, the nucleic acid molecule encodes a polypeptide selected from the group consisting of amino acid residues 26-310 of Nogo receptor-1 as shown in SEQ ID NOs: 7 and 9 or amino acid residues 27-310 of Nogo receptor-1 as shown in SEQ ID NO: 9. As used herein, "nucleic acid" means genomic DNA, cDNA, mRNA and antisense molecules, as well as nucleic acids based on alternative backbones or including alternative bases whether derived from natural sources or synthesized. In some embodiments, the nucleic acid further comprises a transcriptional promoter and optionally a signal sequence each of which is operably linked to the nucleotide sequence encoding the polypeptides of the invention.

In some embodiments, the invention provides a nucleic acid encoding a Nogo receptor-1 fusion protein of the invention. In some embodiments, the nucleic acid encodes a Nogo receptor-1 fusion protein of the invention, including a fusion protein comprising a polypeptide selected from the group consisting of amino acid residues 26-344 of Nogo receptor-1 as shown in SEQ ID NOs: 6 and 8 or amino acid residues 27-344 of SEQ ID NO: 8 and amino acid residues 26-310 of Nogo receptor-1 as shown in SEQ ID NOs: 7 and 9 or amino acid residues 27-310 of SEQ ID NO: 9. In some embodiments, the nucleic acid encoding a Nogo receptor-1 fusion protein further comprises a transcriptional promoter and optionally a signal sequence. In some embodiments, the nucleotide sequence further encodes an immunoglobulin constant region. In some embodiments, the immunoglobulin constant region is a heavy chain constant region. In some embodiments, the nucleotide sequence further encodes an immunoglobulin heavy chain constant region joined to a hinge region. In some embodiments the nucleic acid further encodes Fc. In some embodiments the Nogo receptor-1 fusion proteins comprise an Fc fragment.

The encoding nucleic acids of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Compositions

In some embodiments, the invention provides compositions comprising an immunogenic polypeptide selected from the group consisting of SEQ ID NO: 1, SEQ ID NO: 2, SEQ ID NO: 3, SEQ ID NO: 4 and SEQ ID NO: 5.

In some embodiments, the invention provides compositions comprising an anti-Nogo receptor-1 antibody or an antigen-binding fragment thereof, or a soluble Nogo receptor-1 polypeptide or fusion protein of the present invention.

In some embodiments, the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the molecules of this invention for delivery into the cell. Exemplary "pharmaceutically acceptable carriers" are any and all solvents, dispersion media, coatings, antibacterial and antifungal agents, isotonic and absorption delaying agents, and the like that are physiologically compatible, water, saline, phosphate buffered saline, dextrose, glycerol, ethanol and the like, as well as combinations thereof. In some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the antibodies, antigen-binding fragments, soluble Nogo receptors or fusion proteins of the invention.

Compositions of the invention may be in a variety of forms, including, for example, liquid, semi-solid and solid dosage forms, such as liquid solutions (e.g., injectable and infusible solutions), dispersions or suspensions. The preferred form depends on the intended mode of administration and therapeutic application. In one embodiment, compositions are in the form of injectable or infusible solutions, such as compositions similar to those used for passive immunization of humans with other antibodies.

The composition can be formulated as a solution, micro emulsion, dispersion, liposome, or other ordered structure suitable to high drug concentration. Sterile injectable solutions can be prepared by incorporating the anti-Nogo receptor-1 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See e.g., Sustained and Controlled Release Drug Delivery Systems, J. R. Robinson, ed., Marcel Dekker, Inc., New York, 1978.

Supplementary active compounds also can be incorporated into the compositions. In some embodiments, a Nogo receptor-1 antibody or an antigen-binding fragments thereof, or soluble Nogo receptor-1 polypeptides or fusion proteins of the invention are coformulated with and/or coadministered with one or more additional therapeutic agents.

The pharmaceutical compositions of the invention may include a "therapeutically effective amount" or a "prophylactically effective amount" of an antibody, antigen-binding fragment, polypeptide(s), or fusion protein of the invention. A "therapeutically effective amount" refers to an amount effective, at dosages and for periods of time necessary, to achieve the desired therapeutic result. A therapeutically effective amount of the Nogo receptor-1 antibody or antigen-binding fragment thereof, soluble Nogo receptor-1 polypeptide or Nogo receptor fusion protein may vary according to factors such as the disease state, age, sex, and weight of the individual. A therapeutically effective amount is also one in which any toxic or detrimental effects of the antibody, antigen-binding fragment, soluble Nogo receptor-1 polypeptide or Nogo receptor fusion protein are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody, antigen-binding fragment, and soluble receptor-1 polypeptide or Nogo receptor fusion protein and the particular therapeutic or prophylactic effect to be achieved, and (b) the limitations inherent in the art of compounding such an antibody, antigen-binding fragment, and soluble receptor-1 polypeptide or Nogo receptor fusion protein for the treatment of sensitivity in individuals. In some embodiments a therapeutically effective dose range for Nogo receptor-1 antibodies or antigen-binding fragments thereof is 0.1-4 mg/Kg per day. In some embodiments a therapeutically effective dose range for Nogo receptor-1 antibodies or antigen-binding fragments thereof is 0.2-4 mg/Kg per day. In some embodiments a therapeutically effective dose range for Nogo receptor-1 antibodies or antigen-binding fragments thereof is 0.2 mg/Kg per day.

Uses of the Antibodies, Antigen-Binding Fragments, Soluble Receptors and Fusion Proteins In some embodiments, the invention provides methods for inhibiting Nogo receptor-1 activity by administering anti-Nogo receptor-1 antibodies, antigen-binding fragments of such antibodies, soluble Nogo receptor-1 polypeptides, or fusion proteins comprising such polypeptides to a mammal in need thereof.

In some embodiments, the invention provides a method of inhibiting Nogo receptor-1 binding to a ligand, comprising the step of contacting Nogo receptor-1 with an antibody or antigen-binding fragment of this invention. In some embodiments, the ligand is selected from the group consisting of NogoA, NogoB, NogoC, MAG and OM-gp.

In some embodiments, the invention provides a method for inhibiting growth cone collapse in a neuron, comprising the step of contacting the neuron with the antibody or antigen-binding fragment thereof of this invention. In some embodiments, the invention provides a method for decreasing the inhibition of neurite outgrowth or sprouting in a neuron, comprising the step of contacting the neuron with the antibody or antigen-binding fragment of this invention. In some embodiments, the neuron is a CNS neuron. In some of these methods, the neurite outgrowth or sprouting is axonal growth.

In some embodiments, the invention provides a method of promoting survival of a neuron in a mammal, which neuron is at risk of dying, comprising (a) providing a cultured host cell expressing (i) an anti-Nogo receptor-1 antibody or antigen-binding fragment thereof; or (ii) a soluble Nogo receptor-1 polypeptide; and (b) introducing the host cell into the mammal at or near the site of the neuron. Almudena Ramon-Cueto, M Isabel Cordero, Fernando F Santos-Benito and Jesus Avila (2000) Functional recovery of paralegic rats and motor axon regneration in their spinal cords by olfactory ensheathing cells. Neuron 25, 425-435.

In some embodiments, the invention provides a gene therapy method of promoting survival of a neuron at risk of dying, which neuron is in a mammal, comprising administering at or near the site of the neuron a viral vector comprising a nucleotide sequence that encodes (a) an anti-Nogo receptor-1 antibody or antigen-binding fragment thereof; or (b) a soluble Nogo receptor-1 polypeptide, wherein the anti-Nogo receptor-1 antibody, antigen-binding fragment, or soluble Nogo receptor-1 polypeptide is expressed from the nucleotide sequence in the mammal in an amount sufficient to promote survival of the neuron. Viral vectors and methods useful for these embodiments are described in, e.g., Noël et al., Human Gene Therapy, 13, 1483-93 (2002).

In some embodiments, the invention provides a method of inhibiting Nogo receptor-1 binding to a ligand, comprising the step of contacting the ligand with the soluble Nogo receptor-1 polypeptide or the Nogo receptor-1 fusion protein of this invention.

In some embodiments, the invention provides a method of modulating an activity of a Nogo receptor-1 ligand, comprising the step of contacting the Nogo receptor-1 ligand with a soluble Nogo receptor-1 polypeptide or a Nogo receptor-1 fusion protein of the invention.

In some embodiments, the invention provides a method for inhibiting growth cone collapse in a neuron, comprising the step of contacting a Nogo receptor-1 ligand with a soluble Nogo receptor-1 polypeptide or a Nogo receptor-1 fusion protein of this invention. In some embodiments, the invention provides a method for decreasing the inhibition of neurite outgrowth or sprouting in a neuron, comprising the step of contacting a Nogo receptor-1 ligand with the soluble Nogo receptor-1 polypeptide or the Nogo receptor-1 fusion protein of this invention. In some embodiments, the neuron is a CNS neuron. In some embodiments, the ligand is selected from the group consisting of NogoA, NogoB, NogoC, MAG and OM-gp. In some embodiments, the neurite outgrowth or sprouting is axonal growth.

Any of the types of antibodies or receptors described herein may be used therapeutically. In some embodiments, the anti-Nogo receptor-1 antibody is a human antibody. In some embodiments, the mammal is a human patient. In some embodiments, the antibody or antigen-binding fragment thereof is administered to a non-human mammal expressing a Nogo receptor-1 with which the antibody cross-reacts (e.g., a primate, cynomologous or rhesus monkey) for veterinary purposes or as an animal model of human disease. Such animal models may be useful for evaluating the therapeutic efficacy of antibodies of this invention.

In some embodiments, administration of anti-Nogo receptor-1 antibody or antigen-binding fragment, or soluble Nogo receptor-1 polypeptide or fusion protein is used to treat a spinal cord injury to facilitate axonal growth throughout the injured site.

The anti-Nogo receptor-1 antibodies or antigen-binding fragments, or soluble Nogo receptor-1 polypeptides or fusion proteins of the present invention can be provided alone, or in combination, or in sequential combination with other agents that modulate a particular pathological process. For example, anti-inflammatory agents may be co-administered following stroke as a means for blocking further neuronal damage and inhibition of axonal regeneration. As used herein, the Nogo receptor-1 antibodies, antigen-binding fragments, soluble Nogo receptor-1 and Nogo receptor fusion proteins, are said to be administered in combination with one or more additional therapeutic agents when the two are administered simultaneously, consecutively or independently.

The anti-Nogo receptor-1 antibodies, antigen-binding fragments, soluble Nogo receptor-1 polypeptides, Nogo receptor-1 fusion proteins of the present invention can be administered via parenteral, subcutaneous, intravenous, intramuscular, intraperitoneal, transdermal, inhalational or buccal routes. For example, an agent may be administered locally to a site of injury via microinfusion. Typical sites include, but are not limited to, damaged areas of the spinal cord resulting from injury. The dosage administered will be dependent upon the age, health, and weight of the recipient, kind of concurrent treatment, if any, frequency of treatment, and the nature of the effect desired.

The compounds of this invention can be utilized in vivo, ordinarily in mammals, such as humans, sheep, horses, cattle, pigs, dogs, cats, rats and mice, or in vitro.

Vectors of the Invention

In some embodiments, the invention provides recombinant DNA molecules (rDNA) that contain a coding sequence. As used herein, a rDNA molecule is a DNA molecule that has been subjected to molecular manipulation. Methods for generating rDNA molecules are well known in the art, for example, see Sambrook et al., (1989) Molecular Cloning—A Laboratory Manual, Cold Spring Harbor Laboratory Press. In some rDNA molecules, a coding DNA sequence is operably linked to expression control sequences and vector sequences.

In some embodiments, the invention provides vectors comprising the nucleic acids encoding the polypeptides of the invention. The choice of vector and expression control sequences to which the nucleic acids of this invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable or selectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Examples of such vector plasmids are pUC8, pUC9, pBR322 and pBR329 (Bio-Rad® Laboratories), pPL and pKK223 (Pharmacia). Any suitable prokaryotic host can be used to express a recombinant DNA molecule encoding a protein of the invention.

Expression vectors compatible with eukaryotic cells, preferably those compatible with vertebrate cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Examples of such vectors are pSVL and pKSV-10 (Pharmacia), pBPV-1, pML2d (International Biotechnologies), pTDT1 (ATCC® 31255) and other eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., (1982) J. Mol. Anal. Genet. 1, 327-341). Alternatively, the selectable marker can be present on a separate plasmid, the two vectors introduced by co-transfection of the host cell, and transfectants selected by culturing in the appropriate drug for the selectable marker.

To express the antibodies, or antibody portions of the invention, DNAs encoding partial or full-length light and heavy chains are inserted into expression vectors such that the genes are operatively linked to transcriptional and translational control sequences. Expression vectors include plasmids, retroviruses, cosmids, YACs, EBV-derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In some embodiments, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can be easily inserted and expressed, as described above. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the immunogenic polypeptides, Nogo receptor-1 antibodies, antigen-binding fragments, soluble Nogo receptor-1 polypeptides and soluble Nogo receptor-1 fusion protein of the present invention, the recombinant expression vectors of the invention carry regulatory sequences that control their expression in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the heterologous genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Host Cells and Methods of Recombinantly Producing Protein of the Invention

Nucleic acid molecules encoding anti-Nogo receptor-1 antibodies, immunogenic peptides, soluble Nogo receptor-1 polypeptides, soluble Nogo receptor-1 fusion proteins of this invention and vectors comprising these nucleic acid molecules can be used for transformation of a suitable host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of appropriate cell hosts with a rDNA molecule of the present invention is accomplished by well known methods that typically depend on the type of vector used and host system employed. With regard to transformation of prokaryotic host cells, electroporation and salt treatment methods can be employed (see, for example, Sambrook et al., (1989) Molecular Cloning—A Laboratory Manual, Cold Spring Harbor Laboratory Press; Cohen et al., (1972) Proc. Natl. Acad. Sci. USA 69, 2110-2114). With regard to transformation of vertebrate cells with vectors containing rDNA, electroporation, cationic lipid or salt treatment methods can be employed (see, for example, Graham et al., (1973) Virology 52, 456-467; Wigler et al., (1979) Proc. Natl. Acad. Sci. USA 76, 1373-1376).

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, (1975) J. Mol. Biol. 98, 503-517 or the proteins produced from the cell may be assayed by an immunological method.

Mammalian cell lines available as hosts for expression are well known in the art and include many immortalized cell lines available from the American Type Culture Collection (ATCC®). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 cells. When recombinant expression vectors encoding the immunogenic polypeptides, Nogo receptor-1 antibodies or antigen-binding fragments, soluble Nogo receptor-1 polypeptides and soluble Nogo receptor-1 fusion proteins of the invention are introduced into mammalian host cells, they are produced by culturing the host cells for a period of time sufficient to allow for expression of the antibody, polypeptide and fusion polypeptide in the host cells or, more preferably, secretion of the immunogenic polypeptides, Nogo receptor-1 antibodies or antigen-binding fragments, soluble Nogo receptor-1 polypeptides and soluble Nogo receptor-1 fusion proteins of the invention into the culture medium in which the host cells are grown. Immunogenic polypeptides, Nogo receptor-1 antibodies or antigen-binding fragments, soluble Nogo receptor-1 polypeptides and soluble Nogo receptor-1 fusion proteins of the invention can be recovered from the culture medium using standard protein purification methods.

Further, expression of immunogenic polypeptides, Nogo receptor-1 antibodies or antigen-binding fragments, soluble Nogo receptor-1 polypeptides and soluble Nogo receptor-1 fusion proteins of the invention of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

Host Cells

The present invention further provides host cells transformed with a nucleic acid molecule that encodes a Nogo receptor-1 antibody, antigen-binding fragment, soluble Nogo receptor-1 polypeptide and/or soluble Nogo receptor-1 fusion protein of the invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Examples of useful eukaryotic host cells include Chinese hamster ovary (CHO) cells available from the ATCC® as CCL61, NIH Swiss mouse embryo cells NIH-3T3 available from the ATCC as CRL1658, baby hamster kidney cells (BHK), and the like eukaryotic tissue culture cell lines.

Production of Recombinant Proteins using a rDNA Molecule

The present invention further provides methods for producing an a Nogo receptor-1 antibody or antigen-binding fragment, soluble Nogo receptor-1 polypeptide and/or soluble Nogo receptor-1 fusion protein of the invention using nucleic acid molecules herein described. In general terms, the production of a recombinant form of a protein typically involves the following steps:

First, a nucleic acid molecule is obtained that encodes a protein of the invention. If the encoding sequence is uninterrupted by introns, it is directly suitable for expression in any host.

The nucleic acid molecule is then optionally placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

In order that this invention may be better understood, the following examples are set forth. These examples are for purposes of illustration only and are not to be construed as limiting the scope of the invention in any manner.

EXAMPLE 1

Production of Murine Monoclonal Anti-Nogo Receptor-1 Antibodies

Anti-Nogo receptor-1 antibodies that specifically bind an immunogenic Nogo receptor-1 polypeptide of the invention were made using the following methods and procedures.

Immunizations

Two immunization approaches were used:

1. COS-7 Cells or Cell Membranes Containing Nogo Receptor-1 (NogoR-1) As the Immunogen The rat Nogo receptor-1 gene (GenBank™ No. AF 462390) was subcloned into the mammalian expression vector pEAG1256 (Biogen®) that contained the CMV promotor and geneticin resistance gene for drug selection. The recombinant plasmid was transfected into COS-7 cells using Superfect (Qiagen®). Transfectants were selected using geneticin (Gibco™, 2 mg/ml), cloned and verified for surface expression of Nogo receptor-1 protein by FACS. COS-7 membranes were prepared from these cells according to procedures as described [Wang et al., *J. Neurochem.*, 75:1155-1161 (2000)] with two washings, and stored at 1 mg/ml [protein concentration] in 10% glycerol at −70° C.

Eight-week-old female RBF mice (Jackson Labs, Bar Harbor, Me.) were immunized intraperitoneally either with an emulsion containing 50 µg rat Nogo receptor-1-COS-7 membranes or whole COS-7 cells expressing Nogo receptor-1 on the surface and 50 µl RIBI MPL+TDM+CWS adjuvant (Sigma® Chemical Co., St. Louis, Mo.) once every two weeks (Lipman et al., 1992). Sera from the immunized mice were collected before the first immunization, 7 days after the second and third immunizations, and 38 days after the third immunization and the anti-Nogo receptor-1 antibody titers were measured by ELISA as described below.

2. Specific Nogo Receptor-1 Peptides as the Immunogen

Figure 2:
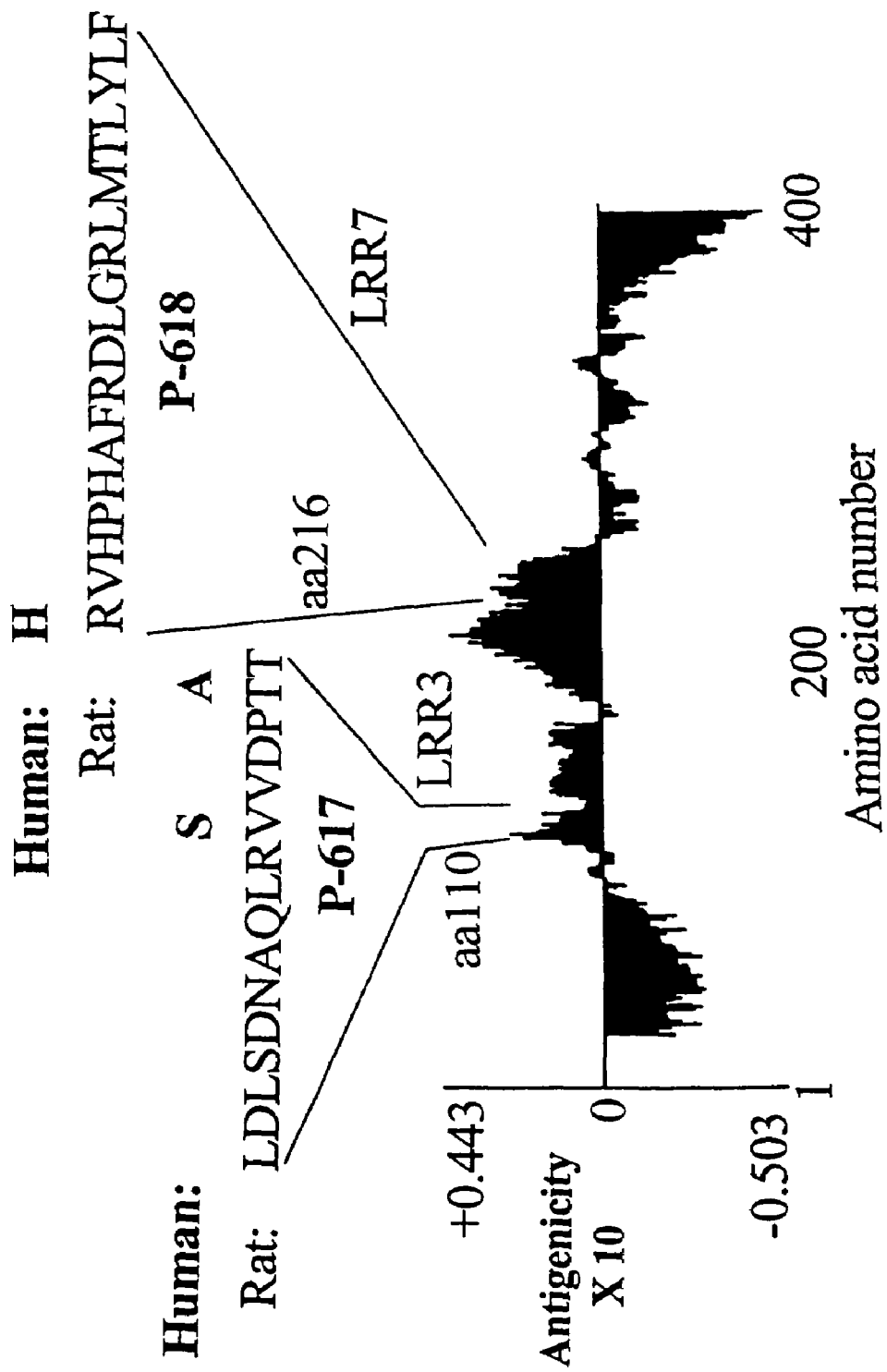
FIG. 2 depicts an antigenicity plot for the Nogo receptor-1 protein using the Vector Nti™ software. Rat P-617 is SEQ ID NO: 10 and rat P-618 is SEQ ID NO: 11.

The rat Nogo receptor-1 gene sequence was subjected to antigenicity analyses using Vector NTi™ software (FIG. 2). Antigenic peptides identified in the analyses were conjugated to Keyhole Limpet Hemocyanin (KLH) using standard glutaldehyde procedures.

Eight-week-old female RBF mice (Jackson Labs, Bar Harbor, Me.) were immunized intraperitoneally with an emulsion containing 50 µg KLH-conjugated peptides and 50 µl complete Freund's adjuvant (Sigma® Chemical Co., St. Louis, Mo.) once every two weeks. Serum from the immunized mice was collected before the first immunization and 1 week after the second and third immunizations and anti-Nogo receptor-1 antibody titers were measured. A booster dose was given after the third immunization. Three days after this booster dose immunization, fusion experiments were initiated.

Hybridoma Production and Screening

Sera from mice immunized with antigenic Nogo receptor-1 peptides were screened by ELISA whereas sera from mice immunized with COS-7 cells expressing Nogo receptor-1 were screened by flow cytometry. Mice that were positive for antibodies that specifically bound Nogo receptor-1-COS-7 cells were identified by flow cytometry and were sacrificed. Splenocytes were isolated from the mice and fused to the FL653 myeloma (an APRT-derivative of a Ig-/HGPRT-Balb/c mouse myeloma, maintained in DMEM containing 10% FBS, 4500 mg/L glucose, 4 mM L-glutamine, and 20 mg/ml 8-azaguanine) as described (Kennett et al., 1993. Monoclonal Antibodies: A New Dimension in Biological Analysis. Plenum Press, New York). Fused cells were plated into 24- or 48-well plates (Corning Glass Works, Corning, N.Y.), and fed with adenine, aminopterin and thymidine containing culture media. AAT resistant cultures were screened by ELISA or flow cytometry for binding to either Nogo receptor-1-COS-7 cells or to a Nogo receptor-1 antigenic peptide as described below. Cells in the positive wells were further subcloned by limiting dilution.

To screen for antibody binding to a Nogo receptor-1 antigenic peptide, the peptides that were used as immunogens were conjugated to BSA. 0.5 µg of the conjugated peptide in 50 µl of 0.1 M sodium bicarbonate buffer, pH 9.0 was added to each well of a 96-well MaxiSorp™ plate (Nunc™). The plate was then incubated at 37° C. for 1 hour or 4° C. for 16 hours and non-specific binding sites were blocked using 25 mM HEPES, pH 7.4 containing 0.1% BSA, 0.1% ovalbumin, 0.1% blotto and 0.001% azide. Hybridoma supernatant was added and incubated at 25° C. for 1 hour. After washing three times with PBS, 50 µl of a 1:10,000 dilution of horseradish peroxidase-conjugated goat anti-mouse secondary antibody (Jackson ImmunoResearch Inc.) was added to each well and incubated further for 1 hour. After three washings, color was developed by TMB (Pierce) and stopped with 2 M sulphuric acid. Color intensity was monitored in a spectrophotometer at 450 .nm.

Antibodies were screened for binding to full length Nogo receptor-1 as follows. COS-7 cells were labeled with 0.1 µM CellTracker™ Green CMFDA (Molecular Probes, Eugene, Oreg.) as described by the vendor. Equal volumes of Cell-Tracker™ labeled control cells were mixed with washed Nogo receptor-1-COS-7 cells before incubation with anti-Nogo receptor-1 test sera. Fifty microliters of the cell mixture was dispensed into each well of a 96-well V-bottom polystyrene plates (Costar® 3877, Corning, N.Y.) and 100 µl of hybridoma supernatant or a control anti-Nogo receptor-1 antibody was added. After incubation at 4° C. for 30 minutes, the cells were washed and incubated with 50 µl of R-phycoerythrin-conjugated affinity pure F(ab')2 fragment goat anti-mouse IgG Fc gamma specific second antibody (1:200, Jackson ImmunoResearch Laboratory, West Grove, Pa.) in PBS. At the end of the incubation, the cells were washed twice with PBS and suspended in 200 µl of PBS containing 1% FBS, and subjected to FACS analyses. Alternately, Nogo receptor-1-COS-7 cells were mixed with hybridoma supernatant and then treated with R-phycoerythrin-conjugated goat anti-mouse secondary antibody and directly subjected to standard FACS analyses.

We generated 25 anti-Nogo receptor-1 antibodies using a variety of immunogens. We generated two antibodies, 7E11 and 5B10, using a peptide sequence corresponding to rat Nogo receptor-1 residues 110-125 as the immunogen. We generated three antibodies, 1H2, 3G5 and 2F7, using membranes prepared from COS7 cells transfected with full length rat Nogo receptor-1 as the immunogen. We generated 13 antibodies using sNogoR310-Fc as the immunogen (1D9.3, 1E4.7, 1B4.3, 2C4.3, 1F10.3, 2H1.4, 1H3.3, 1G4.1, 1E4.1, 2G7.1, 2C4.1, 2F11.1, and 1H4.1) and 7 antibodies using a peptide sequence corresponding to rat Nogo receptor-1 residues 423-434 as the immunogen (2E8.1, 2G11.2, and 1B5.1).

Sequence Analysis of Monoclonal Antibodies 7E11 and 5B10

We extracted total RNA using Qiagen® RNeasy® mini kit, and generated cDNA from the isolated RNA. We amplified the light chain sequence by PCR using primers 5'-TGAG-GAGACGGTGACCGTGGTCCCTTGGCCCCAG-3' (SEQ ID NO: 12) and 5'-AGGTSMARCTGCAGSAGTCWGG-3' (SEQ ID NO: 25). We amplified the heavy chain sequence by PCR using primers 5'-GGGGATATCCACCATGAAGT-TGCCTGTTAGGCTGTTG-3' (SEQ ID NO: 13) and 5'-GGGGATATCCACCATGAGGKCCCCWGCT-CAGYTYCTKGGA-3' (SEQ ID NO: 14). These primers comprise degenerate nucleotides as follows: S represents G or C; M represents A or C, R represents G or A; W represents A or T; K represents G or T; and Y represents T or C. We cloned the PCR fragments into a sequencing vector and determined the DNA sequence of the CDRs by dideoxychain termination using primers specific for the sequencing vector. We conceptually translated the DNA sequences and partial amino acid sequences of the CDR regions of the heavy of light chains of the monoclonal antibodies 7E11 and 5B10 are shown in Table 2. The 3 CDRs from the heavy and light chains of the mAbs are underlined in Table 2. The light chains of 7E11 and 5B10 are have 94% amino acid sequence identity and the heavy chains have 91% amino acid sequence identity. mAbs 7E11, 5B10, and 1H2 are of the IgG1 isotype and mAbs 3G5 and 2F7 are of the IgG2a isotype. Each of these five mAbs has a light chain of the kappa isotype. We analyze the sequence of the other monoclonal antibodies by this approach.

TABLE 2

Amino Acid Sequence of mAbs 7E11 and 5B10

| Sequence | SEQ ID NO: |
|---|---|
| 7E11 Light Chain: MKLPVRLLVLMFWIPASSSDVVMTQTPLSLPVSLGDQ ASISCR<u>SSQSLVHSNGNTYLH</u>WYLQKPGQSPKLLIY<u>K VSNRFS</u>GVPDRFSGSGSGTDFTLKISRVDAEDLGVYF C<u>SQSTHVPFT</u>FGGGTKLEIKRADAAPTVSISHH | 15 |
| 5B10 Light Chain: MKLPVRLLVLMFWIPASSSDVVMTQTPLSLPVSLGDQ ASISCR<u>SSQSLVHSNGYTYLH</u>WYLQRPGQSPKLLIY<u>K VSNRFS</u>GVPDRFSGSGSGTDFTLKISRVDAEDLGVYF C<u>SQSTHVPYT</u>FGGGTKLEIKRADAAPTVSISHH | 16 |

TABLE 2-continued

Amino Acid Sequence of mAbs 7E11 and 5B10

| Sequence | SEQ ID NO: |
|---|---|
| 7E11 Heavy Chain: VQLQESGAELVMPGASVKMSCKASGYTFT<u>DYWMH</u>WVK QRPGQGLEWIG<u>AIDPSDSYSSYNQNFKG</u>KATLTVDGS SSTAYMQLSSLTSEDSAVYYCAR<u>RITEAGAWFAY</u>WGQ GTTVT | 17 |
| 5B10 Heavy Chain: LQXSGAEIVMPGTAVTMSCKASGYTFT<u>DFWMH</u>WVKQR PGQGLEWIG<u>AIDPSDSYSRINQKFKG</u>KATLTVDESSS TAYMQLSSLTSEDSAVYYCAR<u>RITEAGAWFAY</u>WGQGT TVT | 18 |

Inhibition of Ligand Binding to Soluble Nogo receptor-1 by Monoclonal anti-Nogo receptor-1 antibody We tested the anti-Nogo receptor-1 monoclonal antibodies produced as described above to determine whether they inhibited ligand binding to Nogo receptor-1.

Figure 3A:
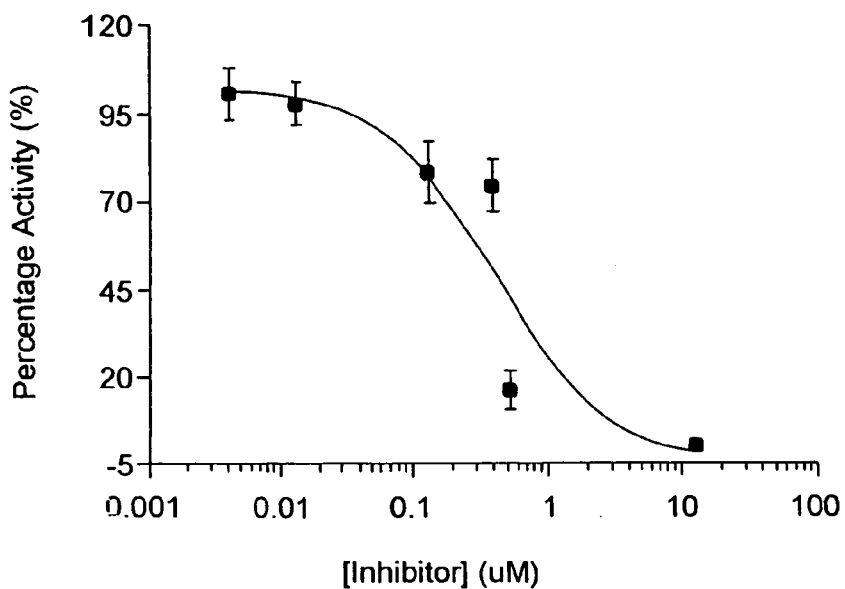
FIG. 3A is a graph depicting the binding activity of anti-Nogo receptor-1 antibody, 7E11. The graph presents the effect of 7E11 concentration on the binding of Nogo66 to Nogo receptor-1.
Figure 3B:
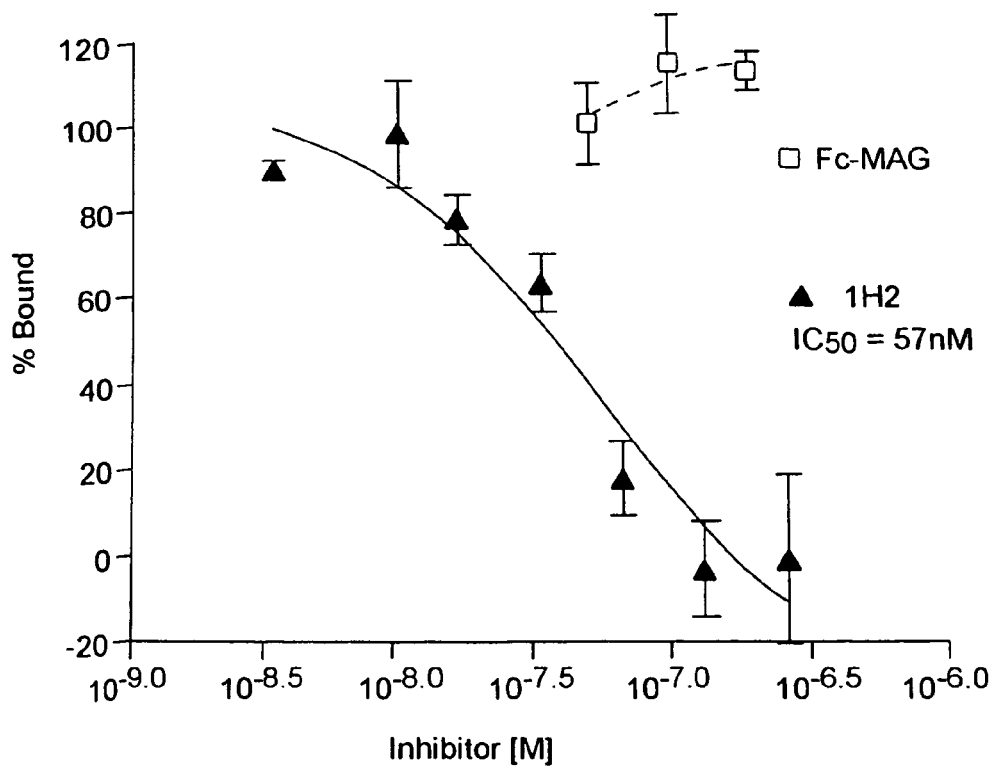
FIG. 3B depicts the binding activity of anti-Nogo receptor-1 antibody, 1H2. The graph presents the effect of 1H2 concentration on the binding of Nogo66 to sNogoR344-Fc (also referred to herein and in U.S. patent application 60/402,866 as Fc-sNogoR344 or Ig-sNogoR344). Fc-MAG did not compete with Nogo66 for binding to sNogoR344-Fc.

0.5 µg of a soluble Nogo receptor-1 fusion protein comprising amino acid residues 26-344 of rat Nogo receptor-1 and the hinge and Fc region of the rat IgG1 molecule (sNogoR344-Fc) produced as described below was immobilized on 250 µg of protein-A- or wheatgerm agglutinin-conjugated SPA beads (Amersham Pharmacia Biotech) for 2 hours at 25° C. SPA beads coupled with Fc-sNogoR-1 [WHICH sNOGO IS THIS?], anti-Nogo receptor-1 mAb and 1 µl $^{125}$I-Nogo66 (Amersham, 2000 Ci/mmol, 1 nM) in 50 µl of the HEPES-buffered incubation medium (10 mM HEPES, pH 7.4, 0.1% bovine serum albumin, 0.1% ovalbumin, 2 mM $MgCl_2$, 2 mM $CaCl_2$ and protease inhibitors) was added to each sample well. After 16 hours, radioactivity was measured in quadruplicate samples using a TopCount® (Packard). $IC_{50}$ values were calculated from a curve-fit analysis (FIG. 3) (PRISM, GraphPad Software, N.J.). In some experiments, we also used AP-ligand conjugates (e.g. AP-Nogo66) and detected binding by monitoring alkaline phosphatase activity. We also assayed the ability of the mAbs to block binding of the ligands MAG-Fc and AP-OM-gp to Nogo receptor-1.

Monoclonal antibodies 7E11, 5B10, 1H2, 3G5 and 2F7 all inhibited binding of Nogo66, MAG and OM-gp to sNogoR344-Fc. The calculated $IC_{50}$ for Nogo66 for 7E11 and 1H2 were 400 nM and 60 nM, respectively. The data from ELISAs monitoring mAb-mediated inhibition of binding of the three ligands to Nogo receptor-1 are summarized in Table 3.

TABLE 3 mAbs Inhibit Binding of Nogo66, MAG and OM-gp to Nogo receptor-1.

| mAb | MAG + sNogoR344-Fc | Nogo66 + sNogoR344-Fc | OM-gp + sNogoR344-Fc |
|---|---|---|---|
| 7E11 | 30 nM (60%) $EC_{50}$ = 0.5 µM | $EC_{50}$ = 1.7 µM | $EC_{50}$ = 150 nM |
| 1H2 | 30 nM (60%) | ND | ND |
| 3G5 | 30 nM (60%) | $EC_{50}$ = 9 nM | ND |
| 2F7 | 30 nM (55%) | $EC_{50}$ = 10 nM | $EC_{50}$ = 5 nM |
| 1D9.3 | 30 nM (70%) $EC_{50}$ = 2.7 nM | $EC_{50}$ = 13 nM | $EC_{50}$ = 5.2 nM |
| 2G7.1 | 30 nM (84%) | $EC_{50}$ = 18 nM | $EC_{50}$ = 1 nM |
| 1E4.1 | 30 nM (75%) $EC_{50}$ = 2.8 nM | — | $EC_{50}$ = 9.1 nM |
| 1G4.1 | 30 nM (90%) $EC_{50}$ = 9.9 nM | — | $EC_{50}$ = 8.2 nM |
| 2C4.1 | 30 nM (50%) | — | ND |

TABLE 3-continued mAbs Inhibit Binding of Nogo66, MAG
and OM-gp to Nogo receptor-1.

| mAb | MAG + sNogoR344-Fc | Nogo66 + sNogoR344-Fc | OM-gp + sNogoR344-Fc |
|---|---|---|---|
| 2F11.1 | 30 nM (45%) | ND | ND |
| 1H4.1 | — | ND | ND |
| 2E8.1 | 30 nM (87%) $EC_{50}$ = 9.2 nM | $EC_{50}$ = 1.5 nM | $EC_{50}$ = 42.9 nM |
| 2G11.2 | 30 nM (80%) | ND | ND |
| 1B5.1 | 30 nM (0%) | ND | ND |

The percent displacement is shown at 30 nM antibody and the $EC_{50}$ for certain mAbs determined from curve-fit analysis as described.
"—" indicates no detectable activity and
"ND" indicates not determined.

EXAMPLE 2

Production of Fab-Phage Anti-Nogo Receptor-1 Antibodies

Anti-Nogo receptor-1 Fab-phage antibodies that specifically bind an immunogenic Nogo receptor-1 polypeptide of the invention were also made by screening a Fab-phage library as follows.

The MorphoSys Fab-phage library HuCAL® GOLD was screened against recombinant rat soluble sNogoR310-Fc protein and COS7 cells expressing rat Nogo receptor-1. Fab-phages that specifically bound to Nogo receptor-1 were purified and characterized. The heavy chain of 14D5 is derived from the $V_H2$ gene and the light chain is derived from the $V_K1$ gene. The amino acid sequences of the CDRs of the heavy chain and light chain of one of these Fab-phages, 14D5, are shown in Table 4.

TABLE 4

Amino Acid Sequence of CDRs of 14D5

| | Amino Acid Sequence | SEQ ID NO: |
|---|---|---|
| Heavy Chain CDR1 | GFSLSTSGGSVG | 19 |
| Heavy Chain CDR2 | LIYSNDTKYYSTSLKT | 20 |
| Heavy Chain CDR3 | SRFWTGEYDV | 21 |
| Light Chain CDR1 | RASQNIAITLN | 22 |
| Light Chain CDR2 | LASSLQS | 23 |
| Light Chain CDR3 | QQYDNYPL | 24 |

14D5 binds to rat Nogo receptor-1 in both monovalent and bivalent forms. In addition, 14D5 binds to mouse and human Nogo receptor-1 and human Nogo receptor-2 but not mouse Nogo receptor-3.

EXAMPLE 3

Immunoprecipitation of Nogo Receptor-1 by Anti-Nogo Receptor-1 Monoclonal Antibodies To perform the immunoprecipitation, 100 µl lysed cells or 50 µl PiPLC treated cells were mixed with 400 or 450 µl extraction buffer [10 mM Tris-HCl, pH 7.2, 0.5% Tween-20™, 0.2 mM PMSF] or RIPA buffer, respectively in the presence of 30 µl Protein A or G and 1-2 µg antibody. The mixture was incubated in a shaker at 4° C. for 16 hours.

Samples were spun gently to pellet the protein A or G coupled beads. The beads were washed three times with 1 ml wash buffer (10 mM Tris-HCl, pH 7.2, 0.1% Tween-20™). The final wash was performed using 10% of original wash buffer.

Beads were resuspended in 100 µl of 2× SDS with 10% beta-mercaptoethanol. Samples were incubated at room temperature before being run on a 4-20% Tris-Glycine gel for SDS-PAGE. As determined by SDS-PAGE gel analysis, monoclonal antibodies, 3G5 and 2F7, immunoprecipitate Nogo receptor-1.

EXAMPLE 4

Determining Antibody Specificity by ELISA

Figure 4:
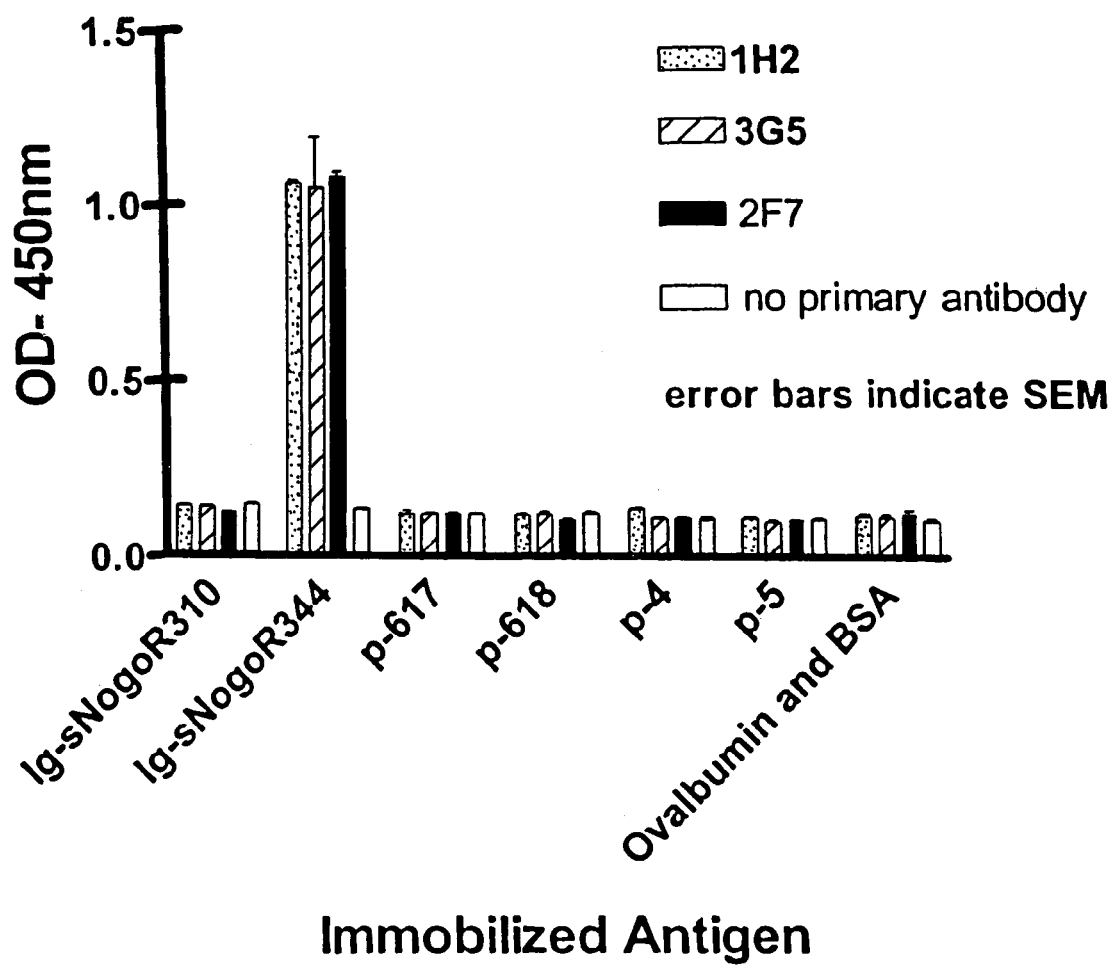
FIG. 4 depicts the results of an ELISA for anti-Nogo-R-1 antibodies 1H2, 3G5 and 2F7. The effect of the antibodies on $OD_{450}$ in the presence of immobilized antigens was determined. The immobilized antigens were sNogoR310-Fc (also referred to herein and in U.S. patent application 60/402,866 as Fc-sNogoR310 or Ig-sNogoR310), sNogoR344-Fc, p-617, p-618, p-4, p-5 and ovalbumin and BSA.

To determine the specificity of the monoclonal and Fab-phage antibodies produced in Examples 1 and 2, we performed an ELISA using a panel of Nogo receptor-1 polypeptides. The panel consisted of sNogoR310-Fc (a fusion protein comprising amino acids 26-310 of rat Nogo receptor-1 and a rat Fc fragment), sNogoR344-Fc (see supra), polypeptide p-617 (SEQ ID NO: 1), polypeptide p-618 (a 19-amino acid polypeptide from the LRR7 region of rat Nogo receptor-1; FIG. 2; SEQ ID NO: 11) and polypeptides p-4 and p-5 (polypeptides from the LRR5 and LRRCT regions of Nogo receptor-1, respectively). Ovalbumin and BSA were used as controls. As shown in FIG. 4, mAbs 1H2, 3G5 and 2F7 all specifically bound to sNogoR344-Fc. In similar experiments, those antibodies also specifically bound a polypeptide consisting of amino acids 310-344 of rat Nogo receptor-1 (SEQ ID NO: 3) and mAbs 7E11 and 5B10 specifically bound polypeptide p-617 (SEQ ID NO: 1).

Ten of the antibodies (1D9.3, 1E4.7, 1B4.3, 2C4.3, 1F10.3, 2H1.4, 1H3.3, 1G4.1, 1E4.1, and 2G7.1) from the sNogoR310-Fc immunization diplaced each other for binding, indicating that they recognize a similar or overlapping epitopes on sNogoR310-Fc. The other three antibodies from the sNogoR310-Fc immunization (2C4.1, 2F11.1, and 1H4.1) recognize different epitopes located in amino acid residues 26-310.

We also performed ELISA binding assays using the Fab-phage 14D5. Where AP-Nogo66, AP-OM-gp and MAG-Fc ligands were allowed to bind to immobilized sNogoR344-Fc, 1 µM 14D5 completely inhibited Nogo and MAG binding. 10 µM of 14D5 was required to completely inhibit the binding of OM-gp to sNogoR344-Fc.

EXAMPLE 5

Neurite Outgrowth Assay

To test the ability of the monoclonal and Fab-phage antibodies produced above to lessen the inhibitory effect of CNS myelin on neurons, Lab-Tek® culture slides (4 wells) were coated with 0.1 mg/ml poly-D-lysine (Sigma®). CNS myelin or PBS was spotted as 3 µl drops. Fluorescent microspheres (Polysciences) were added to the myelin/PBS to allow later identification of the drops (Grandpre et al, Nature 403, 2000). Lab-Tek® slides were then rinsed and coated with 10 µg/ml laminin (Gibco™). Dorsal root ganglions (DRG's) from P3-4 Sprague Dawley rat pups were dissociated with 1 mg/ml collagenase type 1 (Worthington), triturated with fire-polished Pasteur pipettes pre-plated to enrich in neuronal cells and finally plated at 23,000 cells/well on the pre-coated Lab- Tek® culture slides. The culture medium was F12 containing 5% heat inactivated donor horse serum, 5% heat inactivated fetal bovine serum and 50 ng/ml mNGF and incubated at 37° C. and 5% $CO_2$ for 6 hours. Fifteen µg/ml of mAb 7E11 was added immediately after plating.

Slides were fixed for 20 minutes with 4% paraformaldehyde containing 20% sucrose and stained for the neuronal marker anti beta-III-tubulin (Covance TUJ1) diluted 1:500. As secondary antibody anti-mouse Alexa Fluor® 594 (Molecular Probes) was diluted 1:300 and slides were coverslipped with Gel/Mount™ (Biømeda™). 5× digital images were acquired with OpenLab™ software and analysed by using the MetaMorph® software for quantification of neurite outgrowth.

Figure 5:
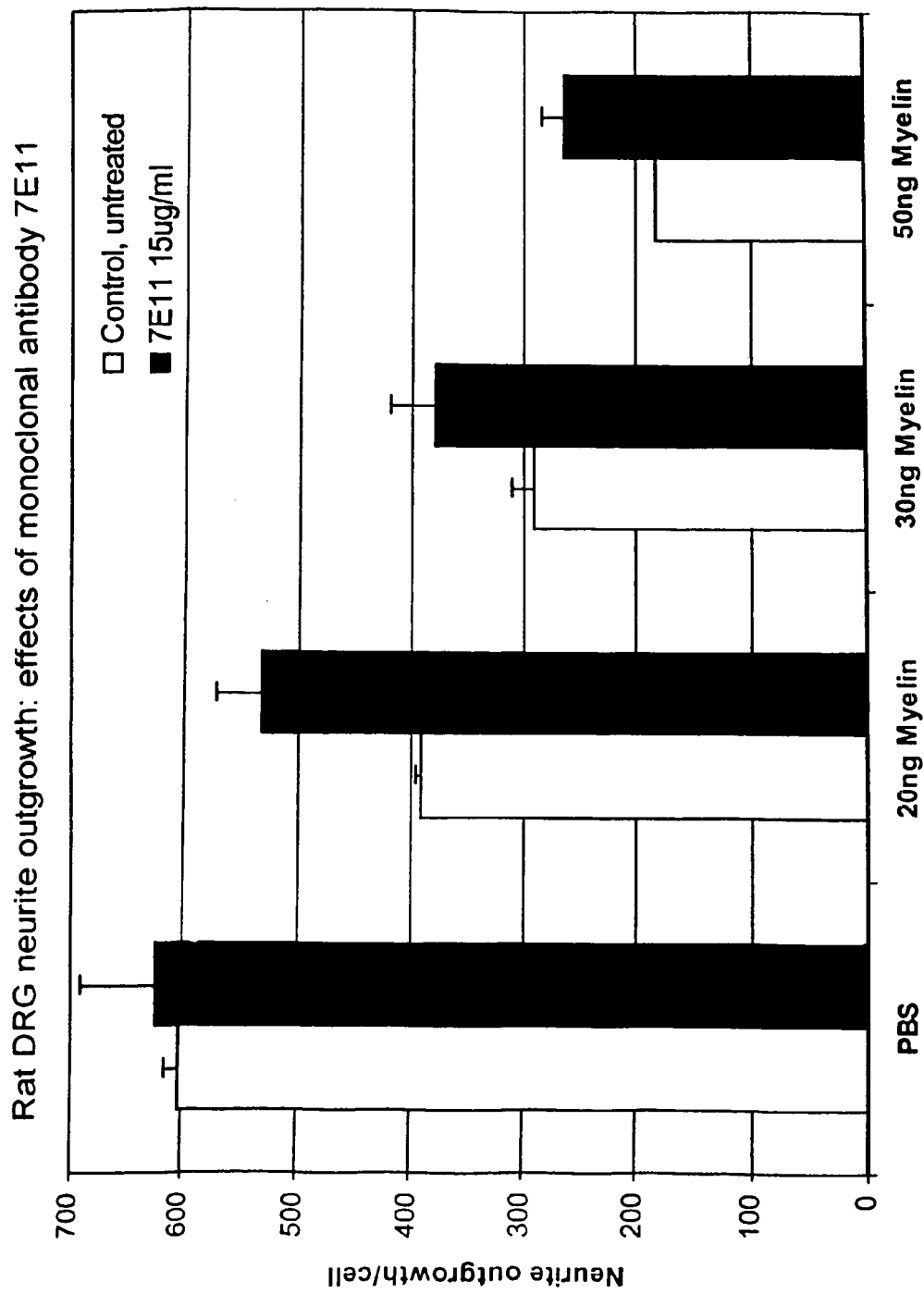
FIG. 5 is a graph depicting the effects of monoclonal antibody, 7E11, on rat DRG neurite outgrowth in the presence of varying amounts of myelin.

MAb 7E11 protected DRG neurons from myelin-mediated inhibition of neurite outgrowth. (FIG. 5). Similar results were observed with mAbs 1H2 and 3G5.

In a neurite outgrowth protection assay where rat P7 DRG neurons were cultured on a CNS myelin substrate, bivalent 14D5 also efficiently promoted neurite outgrowth.

EXAMPLE 6

Immunohistochemistry with 7E11 on Cells Transfected with Nogo Receptor-1

To further characterize the binding properties of anti-Nogo receptor-1 mAbs produced as described in Example 1, we compared binding to both fixed and live COS-7 or 293 cells expressing rat or human Nogo receptor-1.

Fixed Cells:

Nogo receptor-1 transfected and non-transfected cells were plated in 8-well Lab-Tek® culture slides, fixed with 4% paraformaldehyde for 15 minutes, blocked with 10% normal goat serum, 0.1% Triton X-100 in PBS for 1 hour. Mab 7E11 was added at 15 µg/ml and 1.5 µg/ml in blocking solution and incubated for 2 hours at room temperature; Alexa®-conjugated secondary antibody anti-mouse (Molecular Probes) was incubated at a 1:300 dilution in blocking solution for 1 hour; DAPI was added at 5 µg/ml to the secondary antibody to label all nuclei.

Live Cells:

Transfected and non-transfected cells were plated in 8 well Lab-Tek® culture slides, blocked with FACS buffer (containing 4% donor horse serum) for 30 minutes at 4° C., incubated with 7E11 at 15 µg/ml and 1.5 µg/ml in FACS buffer for 1 hour at 4° C., rinsed and incubated with secondary antibody anti-mouse-Alexa® (1:300 in FACS buffer) for 30 minutes at 4° C.

Immunohistochemical staining experiments demonstrated that all of the mAbs bound cells expressing rat Nogo receptor-1. mAbs 7E11, 2G7.1 and 2C4.1 bound both fixed and live cells expressing human Nogo receptor-1.

EXAMPLE 7

Mouse Model of Spinal Cord Contusive Injury

To test the effect of anti-Nogo receptor-1 mAbs produced in Example 1 on neurons in vivo, we use a mouse spinal cord contusion injury model.

Female mice (18-22 g) are treated prophylactically with analgesic and antibiotic agents. Mice are anesthetized and placed in a stereotaxic apparatus with vertebral column fixation under a stereomicroscope. Trauma to the spinal cord is introduced by a modified version of the weight-drop method (M. Li et al., Functional role and therapeutic implications of neuronal caspase-1 and -3 in a mouse model of traumatic spinal cord injury. Neuroscience Vol. 99, pp. 333-342, 2000).

Briefly, a T9 and T10 laminectomy is made and the vertebral column is stabilized using a pair of mouse transverse clamps supporting the T9-T10 transverse processes bilaterally. A stainless steel impact rod with a diameter of 1.4 mm and weight of 2 g, is raised 2.5 cm above the dura and dropped onto the spinal cord at the T10 level. During the surgery, mice are kept on a 37° C. warming blanket and 1 ml of warmed sterile saline is administered subcutaneously to each mouse after surgery to avoid dehydration. The bladder is manually expressed once daily until reflexive bladder control is regained.

All animals receive post-operative analgesia every 8-12 hours after surgery and antibiotic treatment twice daily for 7 days thereafter. Animals have free access to food and water for the duration of the study. Anti-Nogo receptor-1 antibodies are delivered to the injury site via intrathecal injection for 28 days as described in the rat spinal cord transection model below.

EXAMPLE 8

Characterization of Soluble Nogo receptor-1 Fusion Proteins

To characterize soluble Nogo receptor-1 polypeptides (sNogoR-1) and fusion proteins (Fc-sNogoR-1) we performed the following experiment.

Figure 6A:
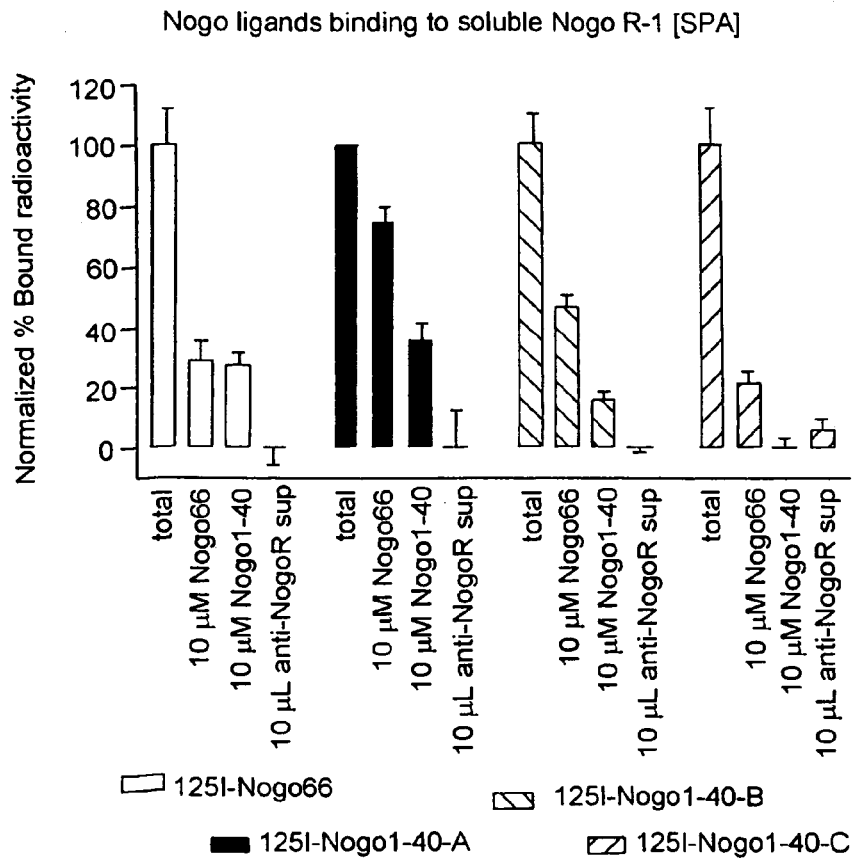
FIG. 6A is a graph depicting the effect of binding of sNogoR310 to $^{125}$I-Nogo66 and $^{125}$I-Nogo40 in the presence of the following competitors: Nogo66, Nogo40 and anti-Nogo receptor-1 monoclonal antibody supernatant.
Figure 6B:
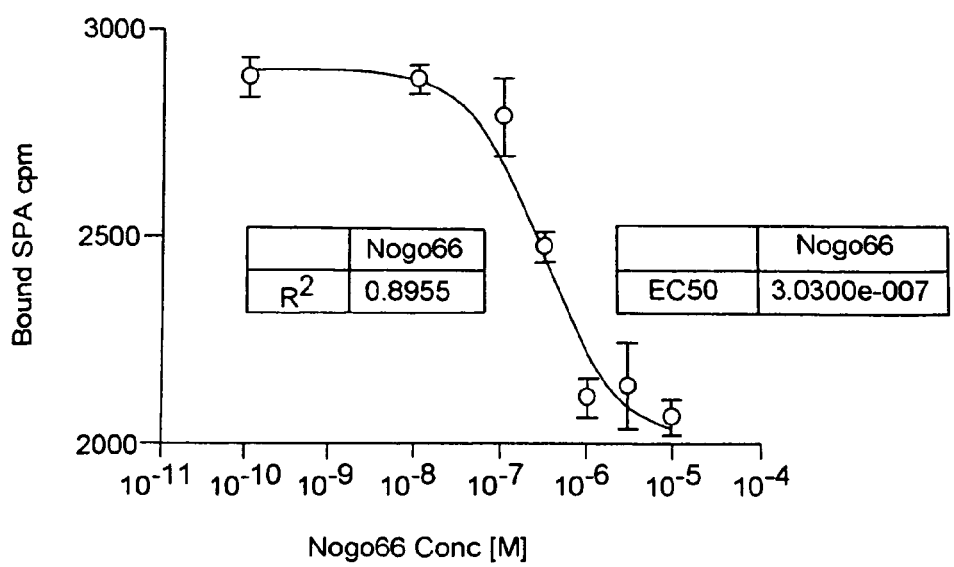
FIG. 6B depicts the binding activity of $^{125}$I-Nogo66 to sNogoR310.
Figure 7:
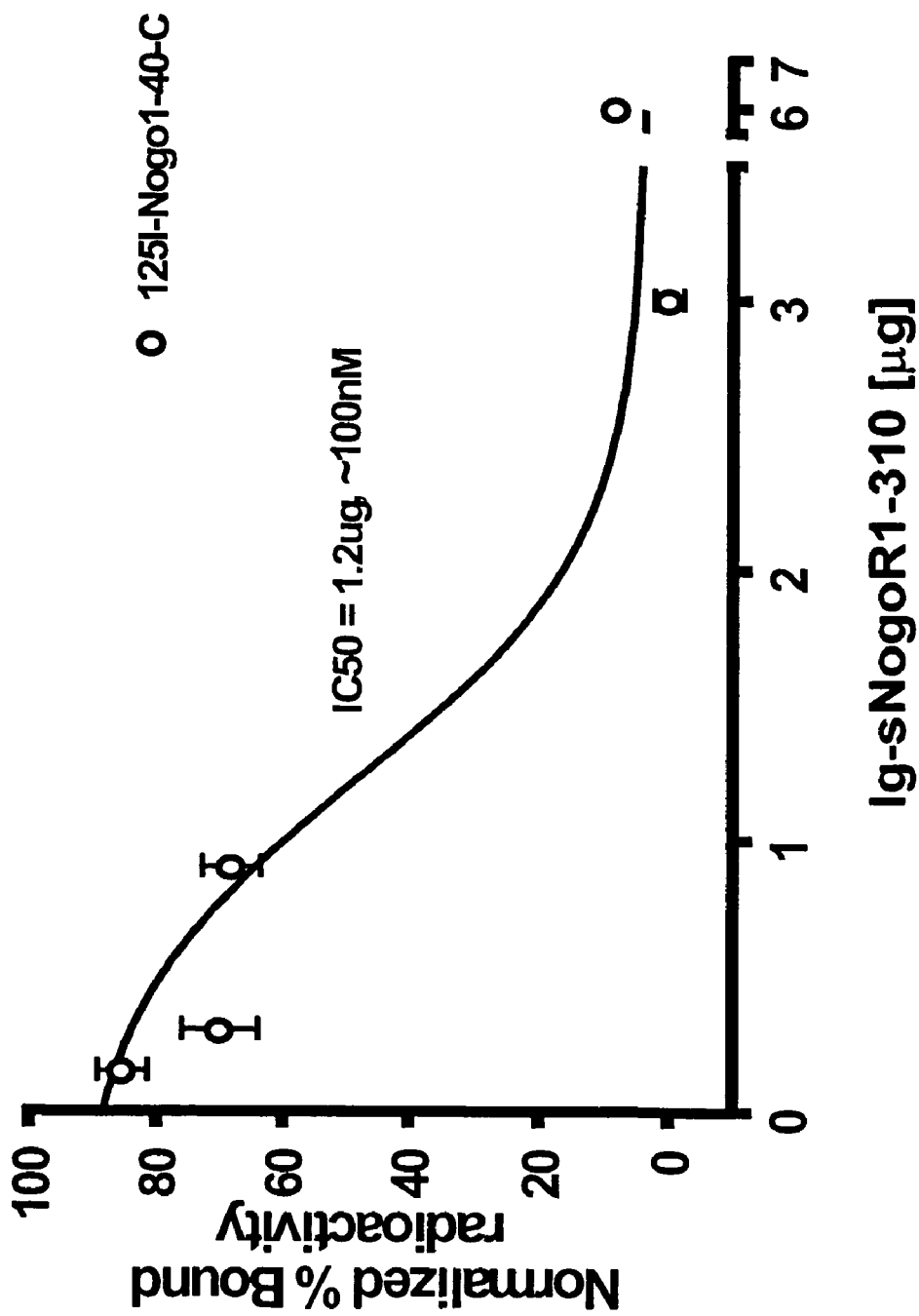
FIG. 7 is a graph depicting the effect of sNogoR310-Fc on $^{125}$I-Nogo40 binding to sNogoR310.
Figure 8:
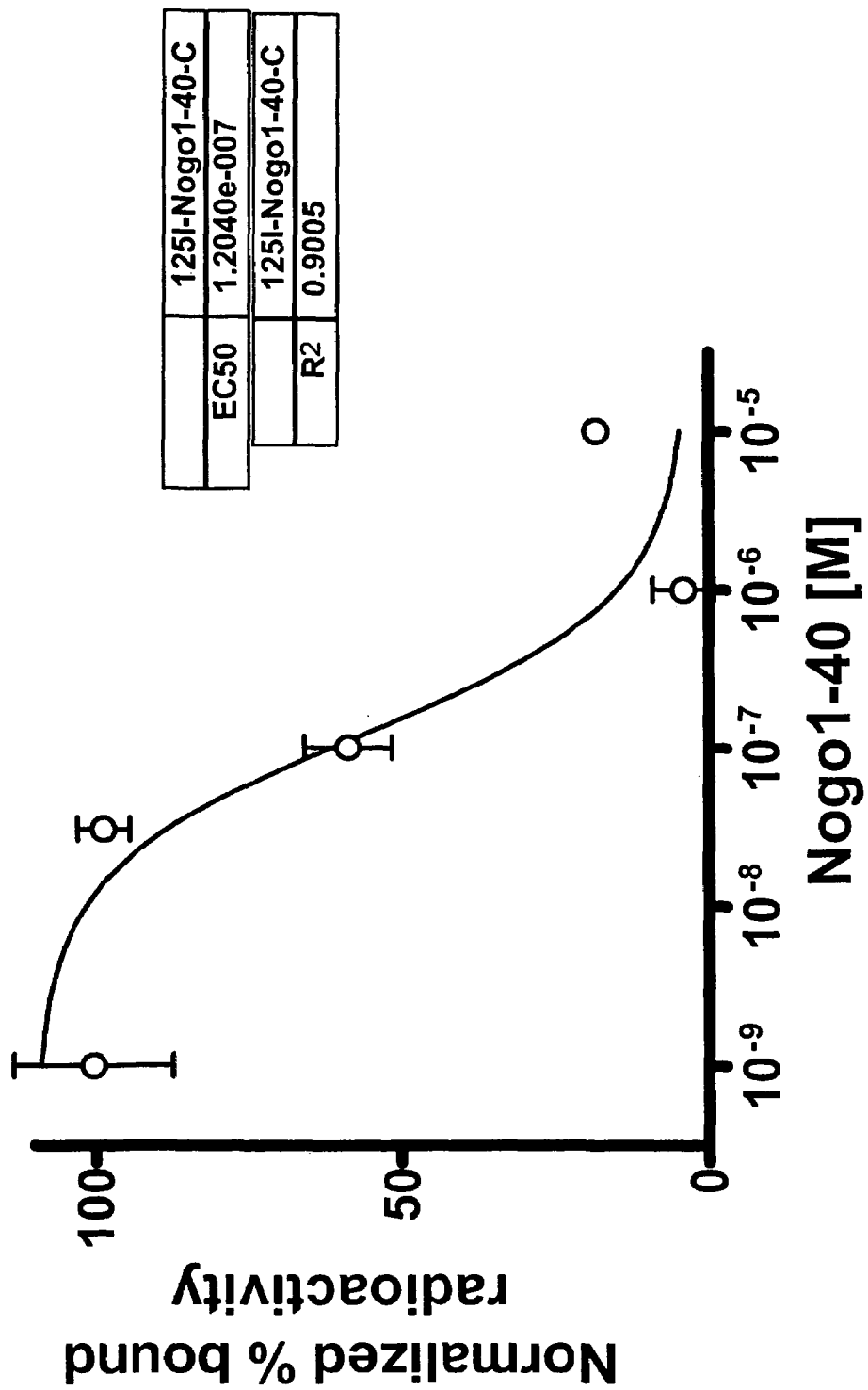
FIG. 8 is a graph depicting the binding activity of sNogoR310-Fc to $^{125}$I-Nogo40.

Three µg of soluble Nogo receptors (sNogoR310-Fc and sNogoR344-Fc) were immobilized on 250 µg WGA-SPA beads and received 0.5 µL of radioactive ligand (final concentration 0.5 nM) in a final volume of 100 µL of binding buffer (20 mM HEPES, pH 7.4, 2 mM Ca, 2 mM Mg, 0.1% BSA, 0.1% ovalubmin and protease inhibitors). Ligands included 10 µM Nogo66, 10 µM $^{125}$I-Nogo40(amino acids 1-40 of NogoA) and 10 µL of anti-Nogo receptor-1 antibody supernatant for each ligand set. The three tyrosines on Nogo40 were separately iodinated and designated as Nogo40-A, -B and -C respectively. Mean values of triplicates are presented as normalized % bound radioactivity (FIGS. 6, 7 and 8). Error bars indicate SEM. Bound radioactivity in the absence of inhibitors was taken as 100% and the lowest bound radioactivity in the presence of 10 µM Nogo40 was taken as the 0% for data normalization.

EXAMPLE 9

Inhibition of Ligand Binding to Soluble Nogo receptor-1 Fusion Protein

A binding assay similar to the binding assay of Example 8 was used to test the ability of two mAbs produced in Example 1 to inhibit $^{125}$I-Nogo66 binding to sNogoR344-Fc. Mabs 2F7 and 3G5 inhibited $^{125}$I-Nogo66 binding to sNogoR344-Fc.

EXAMPLE 10

Neurite Outgrowth Assay

Lab-Tek® culture slides (4 wells) were coated with 0.1 mg/ml poly-D-lysine (Sigma®). CNS myelin alone or mixed with sNogoR310, sNogoR310-Fc fusion protein, mAb 5B10 or control PBS were separately spotted as 3 µl drops. Fluorescent microspheres (Polysciences) were added to the myelin/PBS to allow later identification of the drops (Grandpre et al, Nature 403, 2000). Lab-Tek® slides were then rinsed and coated with 10 µg/ml laminin (Gibco™)

Dorsal root ganglions (DRG's) from P3-4 Sprague Dawley rat pups were dissociated with 1 mg/ml collagenase type 1 (Worthington), triturated with fire-polished Pasteur pipettes pre-plated to enrich in neuronal cells and finally plated at 23,000 cells/well on the pre-coated Labtek culture slides. The culture medium was F12 containing 5% heat inactivated donor horse serum, 5% heat inactivated fetal bovine serum and 50 ng/ml mNGF and incubated at 37° C. and 5% $CO_2$ for 6 hours.

Figure 9A:
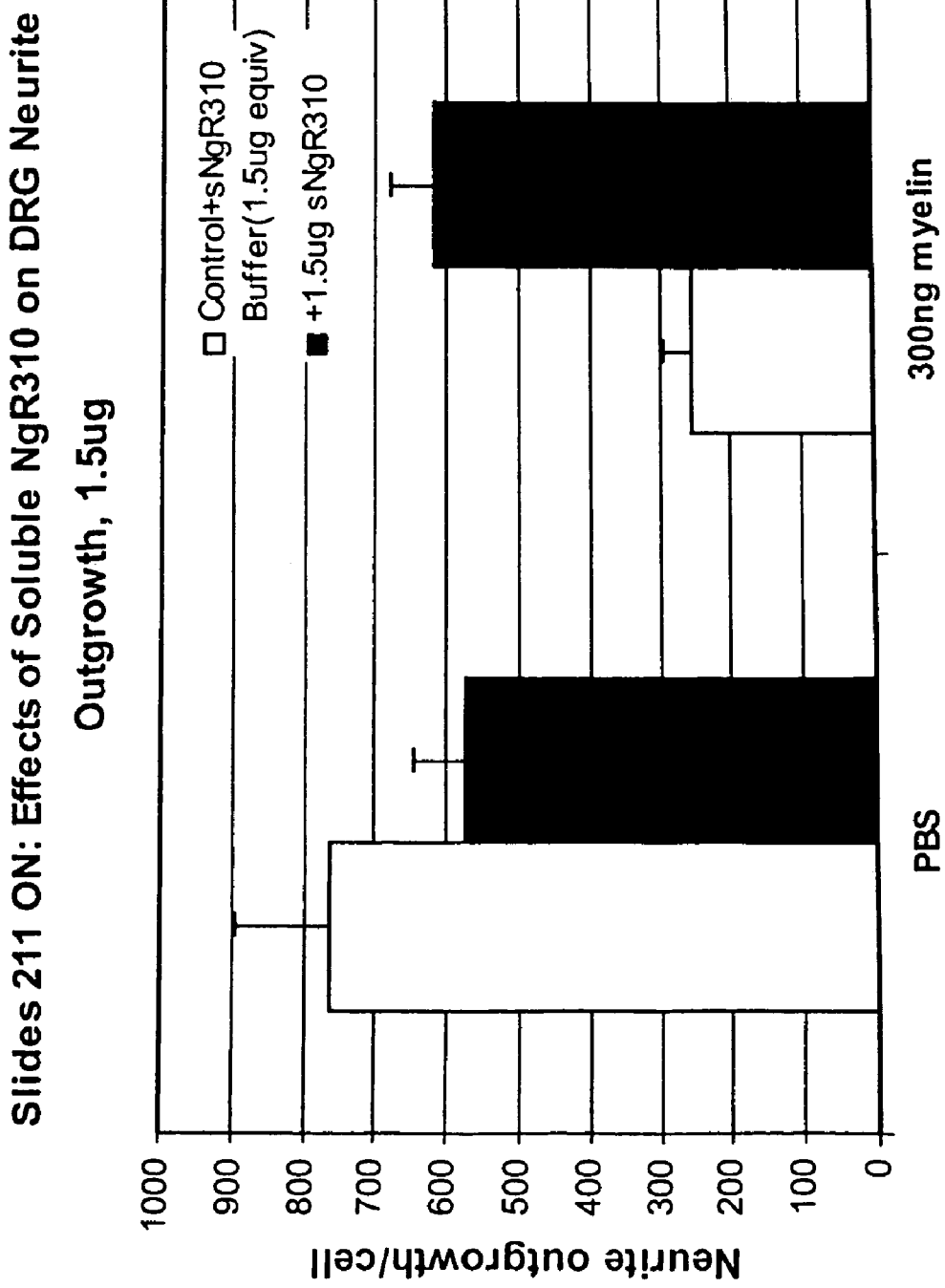
FIG. 9A is a graph of the effect of sNogoR310 on neurite outgrowth/cell in the presence or absence of myelin.
Figure 9B:
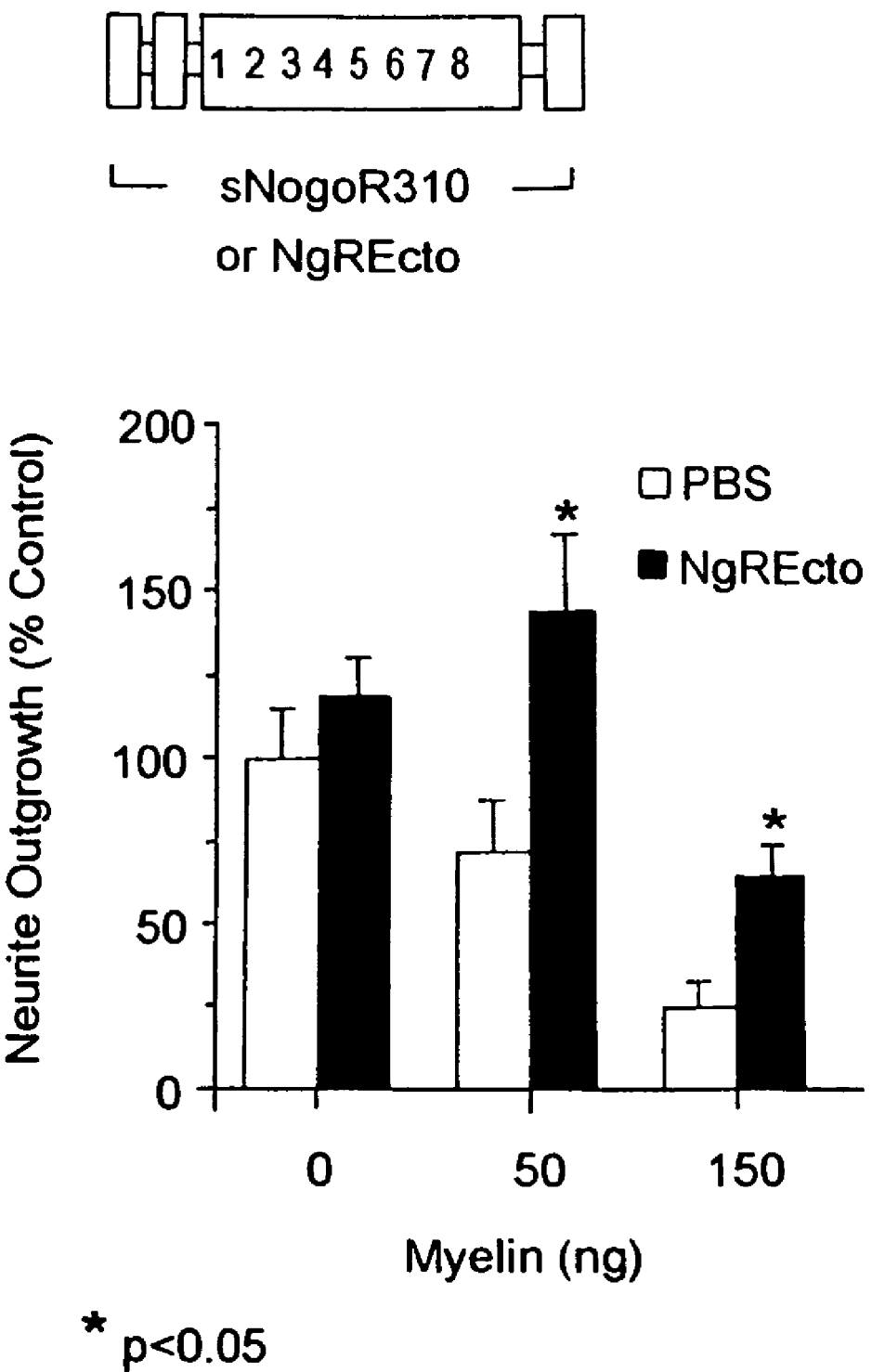
FIG. 9B is a graph of the effect of sNogoR310 on neurite outgrowth in the presence or absence of myelin.
Figure 10B:
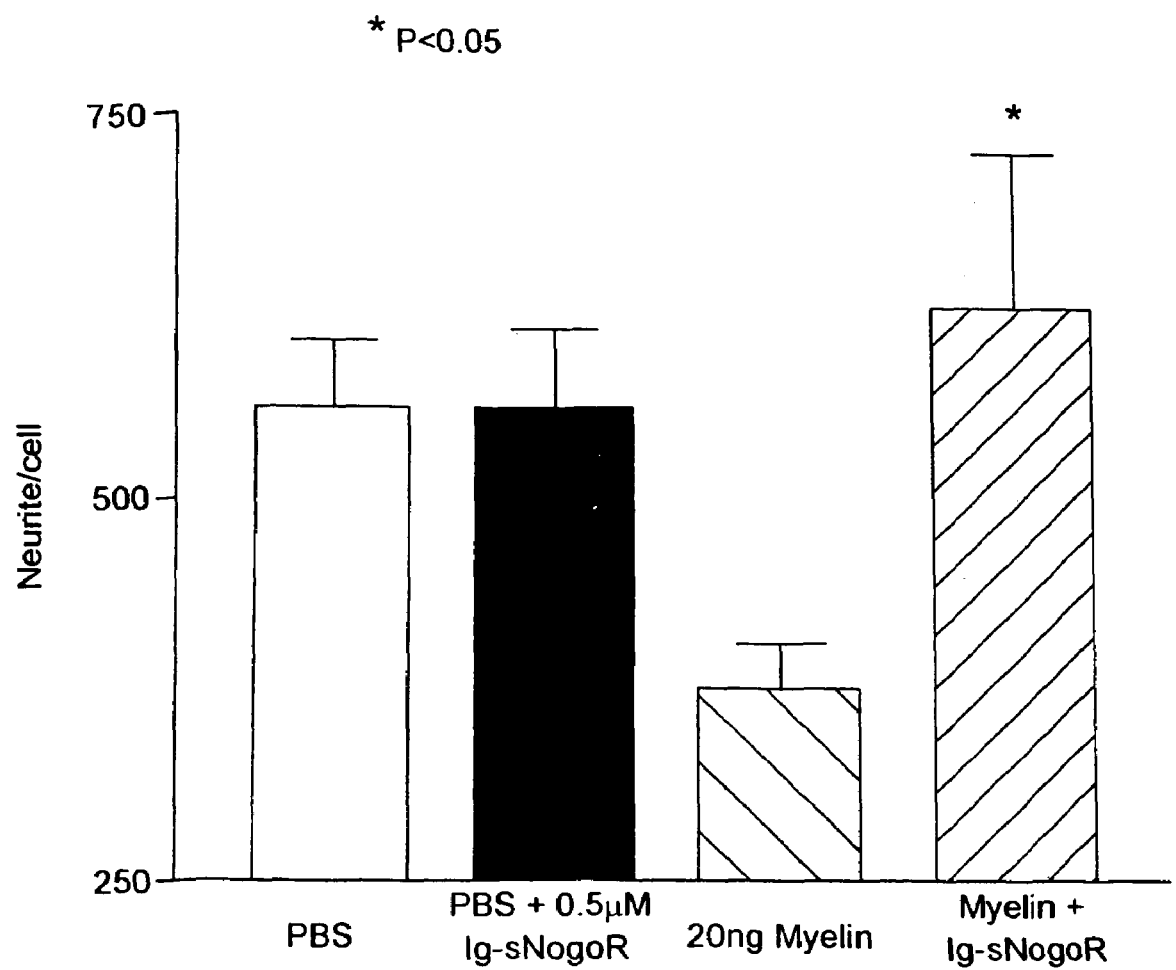
FIG. 10B depicts the number of neurites/cell following treatment with PBS, PBS+sNogoR310-Fc, 20 ng myelin and myelin+sNogoR310-Fc.
Figure 11:
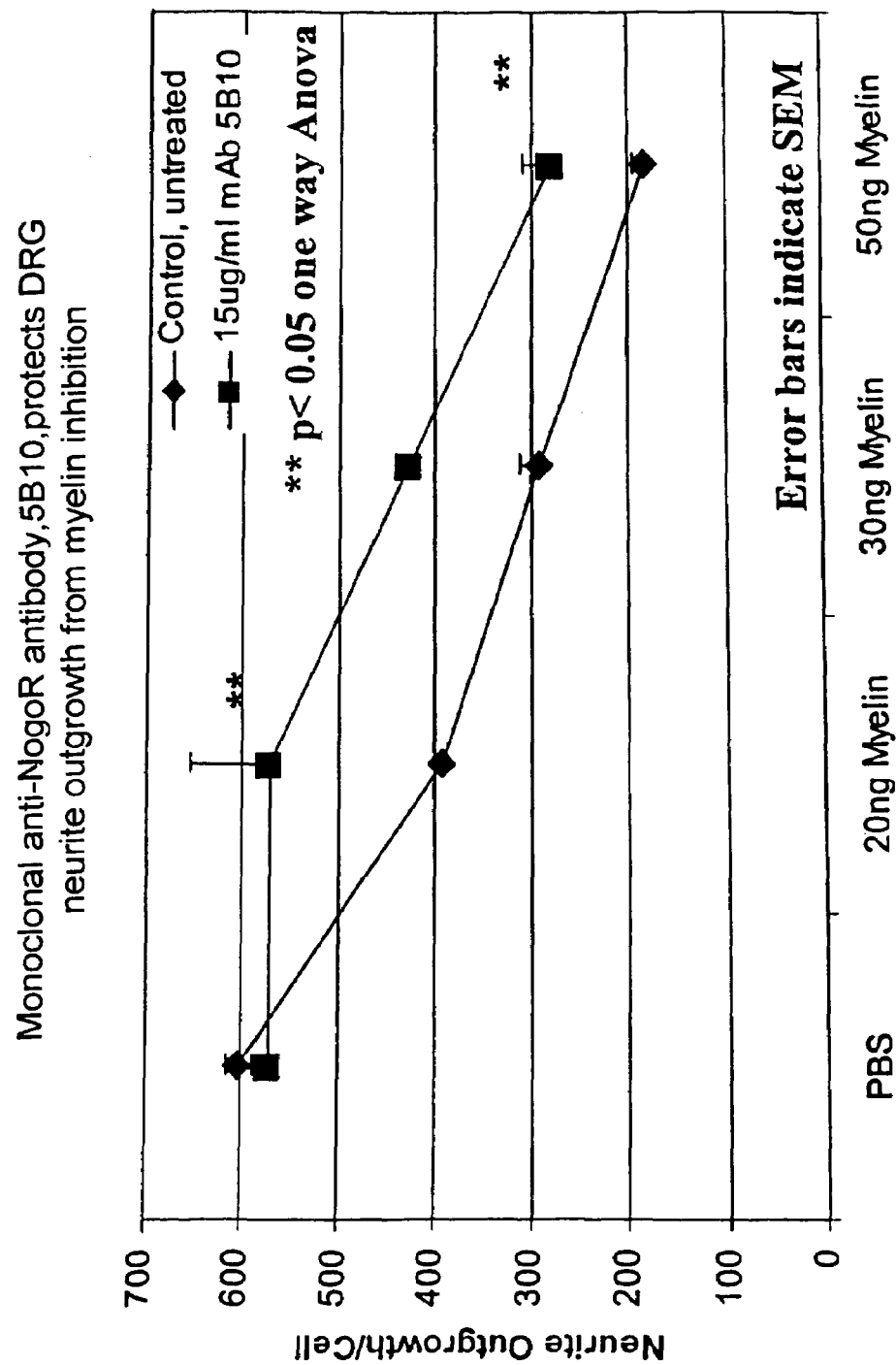
FIG. 11 is a graph depicting the effect of monoclonal antibody 5B10 on DRG neurite outgrowth/cell in the presence of increasing amounts of myelin.

Slides were fixed for 20 minutes with 4% paraformaldehyde containing 20% sucrose and stained for the neuronal marker anti beta-III-tubulin (Covance TUJ1) diluted 1:500. As secondary antibody anti-mouse Alexa Fluor® 594 (Molecular Probes) was diluted 1:300 and slides were cover-slipped with Gel/Mount™ (Biømeda™). 5× digital images were acquired with OpenLab™ software and analyzed by using the MetaMorph® software for quantification of neurite outgrowth.

sNogoR310, sNogoR310-Fc and mAb 5B10 all protected DRG neurons from myelin-mediated inhibition of neurite outgrowth (FIGS. 9-11). sNogoR310 was used in a similar assay using chick neurons and was found to be protective.

We also tested the neuro-protective effect of soluble Nogo receptors by performing experiments with cells grown in the presence and absence of laminin. Neuronal cell growth in media without laminin is poor and models neuronal stress conditions.

DRG's were dissected from post-natal day 6-7 rat pups (P6-7), dissociated into single cells and plated on 96-well plates pre-coated with poly-D-lysine as described above. In some wells 2 µg/ml laminin was added for 2-3 hours and rinsed before the cells were plated. After an 18-20 h incubation the plates were fixed with 4% para-formaldehyde, stained with rabbit anti-Beta-III-tubulin antibody diluted 1:500 (Covance®) and anti-HuC/D diluted 1:100 (Molecular Probes), and fluorescent secondary antibodies (Molecular Probes) were added at 1:200 dilution. The ArrayScan® II (Cellomics®) was used to capture 5× digital images and to quantify neurite outgrowth as average neurite outgrowth/neuron per well, by using the Neurite outgrowth application. Nine 5× images from 3 wells/condition were analyzed.

In some experiments, a sub-clone of PC12 cells (Neuroscreen™) was used (Cellomics®). The Neuroscreen™ cells were pre-differentiated for 7 days with 200 ng/ml NGF, detached and replated on 96-well plates pre-coated with poly-D-lysine. In some wells 5 µg/ml laminin was added for 2-3 hours and rinsed before the cells were plated. After 2 days incubation the plates were fixed with 4% para-formaldehyde, stained with rabbit anti-Beta-III-tubulin antibody diluted 1:500 (Covance®) and Hoechst (nuclear stain). The ArrayScan® II was used to quantify neurite outgrowth as in the DRG cells.

sNogoR344-Fc or rat IgG were added in solution to P6-7 DRG neurons and to differentiated Neuroscreen™ cells at the time of plating.

The neuro-protective effect of sNogoR344-Fc was observed at 1 µM and 10 µM when P6 DRG neurons were grown in the absence of laminin. Quantification of neurite outgrowth showed a dose-dependent increase with the addition of sNogoR344-Fc. Addition of sNogoR344-Fc at the same concentrations to DRG neurons growing on a laminin substrate, did not produce any unusual effect, indicating that sNogoR344-Fc is only active on stressed cells. The neuro-protective effect of sNogoR344-Fc at the same concentrations in the absence of laminin also was seen with Neuroscreen™ cells.

EXAMPLE 11

Production and Purification of Fc-sNogoR-1 Fusion Protein

A cDNA construct encoding amino acids 1-310 of rat Nogo receptor-1 was fused to rat IgG1 Fc contained in a mammalian expression vector and this vector was electroporated into Chinese hamster ovary (CHO) (DG44) cells. Cells were maintained in alpha-MEM, supplemented with 10% dialyzed fetal bovine serum, 2 mM glutamine and antibiotic-antimycotic reagents. Two days after transfection, the conditioned media was collected and analyzed by Western blot under reducing conditions. A protein band about 60 kDa was detected using a polyclonal rabbit anti-Nogo receptor-1 antibody. Cells were expanded and sorted using a R-PE conjugated goat anti-rat IgG antibody. After the second sorting, cells were plated at a density of one cell/well in 96-well plates. Secreted soluble Nogo receptor-1 protein levels from individual wells was tested and compared using a Sandwich ELISA. ELISA plate was coated with goat anti-rat IgG FCK specific antibody. Conditioned media was applied. The bound soluble Nogo receptor-1 protein was detected by HRP conjugated donkey anti-rat IgG Fab, Fc-specific antibody. Clone 4C12 had the highest secretion level. 4C12 was expanded and grown in CHO-M7 media in spinner flask. The secretion level was about 10 mg/L at 37° C.

CHO cells expressing the sNogoR310-Fc fusion protein were cultured in large scale. 1.7 L of concentrated conditioned media was obtained from a 10 L bioreactor run. The pH was raised by addition of one-tenth volume 1.0 M Tris-HCl, pH 8.9. Solid sodium chloride and glycine were added to 3.0 M and 1.5 M respectively. A 60 mL protein A-Sepharose™ column equilibrated with 10 mM Tris-HCl, 3 M sodium chloride, 1.5 M glycine, pH 8.9 was prepared. Concentrated conditioned media was applied to the column at 1.5 mL/min using a peristaltic pump. The column was washed with 300 mL of 10 mM Tris-HCl, 3 M sodium chloride, 1.5 M glycine, pH 8.9 followed with 120 mL 5 mM Tris-HCl, 3 M sodium chloride, pH 8.9. Protein was eluted with 25 mM sodium phosphate, 100 mM sodium chloride, pH 2.8. 10 mL fractions were collected in tubes containing 1.0 mL of 1.0 M HEPES, pH 8.5. Protein fractions were pooled and dialyzed against 3×2 L of 5 mM sodium phosphate, 300 mM NaCl, pH 7.4.

EXAMPLE 12

Spinal Cord Transection Assay

To test their ability to promote functional recovery in vivo, an sNogoR-1 fusion protein was tested in a rat spinal cord transection assay.

Alzet® osmotic pumps were loaded with test solution (sNogoR310-Fc in PBS) made up freshly on the day of use. The loading concentration was calculated to be 5 and 50 µM. Pumps were primed for >40 hours at 37° C. prior to implantation into animals. Female Long Evans rats were given pre-operative analgesia and tranquilizer and anesthetized using isoflurane (3% in $O_2$).

Rats were placed in a stereotaxic frame and the motor cortex exposed for infusion of the tract tracing agent BDA (10,000 MW) bilaterally. Rats then underwent dorsal hemisection of the spinal cord at T5-T6 followed by implantation of the intrathecal catheter and pump system to deliver test compound (n=11 per group).

Rats were allowed to recover and survive up to 28 days after surgery. Behavioral scoring using the BBB system was recorded up to 28 days after induction of injury, just prior to termination of the in-life phase of the study. Following perfusion and fixation, spinal cords were removed, cryoprotected, sectioned, stained and axonal counts performed.

Figure 12:
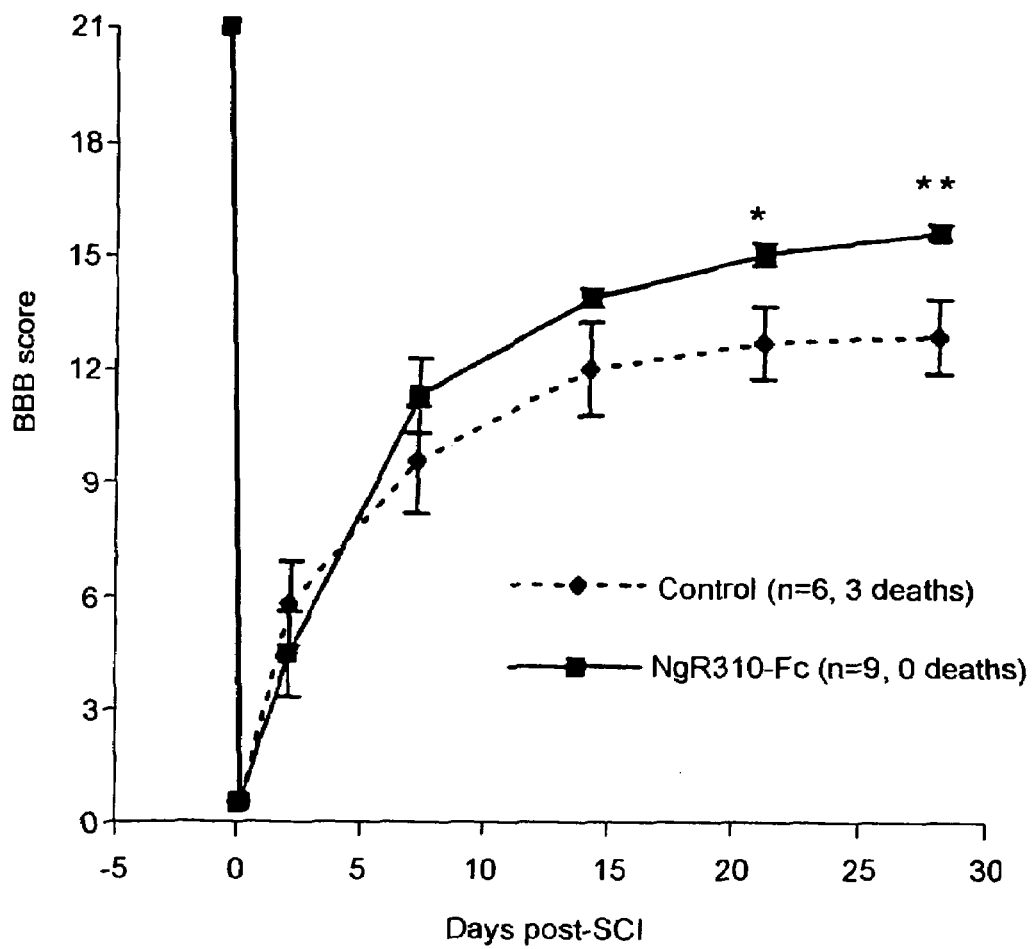
FIG. 12 is a graph depicting the effect of sNogoR310-Fc on the BBB score up to 30 days following induction of injury in a rat spinal cord transection model.

The Basso-Beattie-Bresnahan (BBB) locomotor rating scale (Basso et al., 1996, Neurotrauma 13, 343-359), the inclined plane test and the inclined grid walking test (Li and Strittmatter, 2003, J. Neurosci. 2003, 23, 4219-27) were monitored in rats and mice after injury. For the inclined plane test, we measured the maximal angle to which a 50 cm×60 cm board could be angled for 5 sec without the mouse sliding off. For inclined grid walking, the mice were trained to climb a wire grid (35 cm long with 2.54 cm squares) at a slope of 45 degrees. The number of instances in which the hindpaw dropped below the grid plane was scored for each excursion from bottom to top. For the rat behavioral testing, BBB locomotor scale, grid walking and footprint analysis were performed. For grid walking, the rats were trained to walk on a wire grid (70 cm long with 2.54 cm squares), and the number of instances in which the hindpaw dropped below the grid plane was counted. For footprint analysis, the walking patterns of rat hindpaws were recorded with ink during a continuous locomotion across a 90 cm runway, and stride length on each side and stride width were calculated (Metz et al., 2000, Brain Res., 883, 165-177). All of these behavioral tests were performed by at least two individuals. Throughout the surgery, behavioral testing and histologic analysis, researchers were blind to the identity of the compound in the minipump.

sNogoR310-Fc promoted functional recovery (FIG. 12).

EXAMPLE 13

Rat Spinal Cord Contusion Assay

The effect of soluble Nogo receptor-1 polypeptides and fusion proteins on neurons in vivo are tested in a rat spinal cord contusion assay.

Female hooded Long Evans rats (170-190 g) are treated prophylactically with analgesic and antibiotic agents. Ten minutes before surgery, animals are tranquilized with 2.5 mg/kg Midazolam i.p. and anesthetized in 2-3% isoflurane in $O_2$. Rats are then shaved, wiped down with alcohol and betadine, and ocular lubricant applied to their eyes. Next, an incision is made down the midline and the T7 to T12 vertebrae exposed.

A dorsal laminectomy is performed at T9 ½ and T10 to expose the cord. The rat is mounted on the Impactor. T7 and T8 segments are first clamped and then the T11 and T12 segments are attached to the caudal clamp. A soft material is placed underneath the chest of the rat. The Impactor rod is set to the zero position and the electrical ground clip is attached to the wound edge. The Impactor rod is then raised to 25.0 mm and appropriately adjusted to a position directly above the exposed spinal cord. Next, the Impactor rod is released to hit the exposed cord and the Impactor rod is immediately lifted.

The rat is then dismounted, and Gelfoam® placed on the wound. The muscle over the wound is sutured, and the incision is surgically stapled. Animals are placed in an incubator until they recover from anesthesia. Rats are given antibiotics, analgesics, and saline as required. Bladders are expressed every morning and evening thereafter until function is recovered.

Soluble Nogo receptor-1 fusion protein (e.g., sNogoR310-Fc) is administered intrathecally as described in the rat spinal cord transection model above. BBB scoring is performed one-day after surgery, then every week thereafter until 4 to 6 weeks.

EXAMPLE 14

Expression of sNogoR310 in Transgenic Mice

We produced transgenic mice expressing soluble Nogo receptor-1 protein to test its effect when expressed in vivo.

We cloned the mouse sNogoR310 cDNA (corresponding to amino acids. 1-310 of the Nogo receptor-1) into the NotI site of the C-3123 vector. In this vector, sNogoR310 expression is under the control of the glial fibrillary acidic protein (gfap) gene regulatory elements, which allow high level expression with enhanced secretion from reactive astrocytes at site of injury. We digested the resulting vector sequentially with AatII and SfiI and isolated the gfap::sNogoR310 construct on a 3.4 kb fragment. We microinjected this fragment into embryos to generate transgenic mice. We verified by PCR that the transgene had integrated and identified five founder lines. We crossed heterozygous males of the two founder lines with the highest expression levels to female C57BL/6J mice. We confirmed that the GFAP-positive cells express and secrete sNogoR310 in heterozygous transgenic mice by Western blot analysis using antibody raised against Nogo receptor-1.

We homogenized the cortex and spinal cord in Tris-buffered saline supplemented with protease inhibitors (Roche) and centrifuged the homogenate at 40,000 rpm for 20 min at 4° C. We treated the supernatant with 4% paraformaldehyde for 20 min to enhance antibody specificity and dialyzed prior to immunoblotting. We homogenized the particulate fraction by sonication in RIPA buffer (1% Triton® X-100, 0.5% sodium deoxycholate, 0.1% SDS in PBS), centrifuged the resulting homogenate and treated this supernatant (detergent-soluble particulate fraction) as above. We analyzed 20 µg of brain or spinal cord protein by immunoblot using rabbit antiserum raised against Nogo receptor-1 at 1:2000 dilution. We visualized immunoreactivity by incubation with AP-conjugated anti-rabbit IgG and NBT/BCIP AP substrates.

We detected secreted 37 kDa sNogoR310 in detergent-free soluble extracts of cortex and spinal cord from the two transgenic lines Tg08 and Tg01, but little if any soluble Nogo receptor-1 protein at 37 or 81 kDa is present in littermate wild type (WT) mice. Examination of the particulate fractions demonstrated that there were comparable levels of endogenous Nogo receptor-1 in both WT and transgenic mice.

EXAMPLE 15

Expression of sNogoR310 in Transgenic Mice After Injury

We tested the effect of CNS injury on sNogoR310 expression in transgenic mice by performing a dorsal over-hemisection injury. We obtained sNogoR310 transgenic and non-transgenic control animals by mating heterozygous males with C57/BL6 females as described in Example 14.

We deeply anesthetized adult female heterozygous transgenic or littermate WT mice (10-16 weeks of age) and performed a complete laminectomy, fully exposing the dorsal part of spinal cord at T6 and T7 levels. We performed a dorsal over-hemisection at T6 with a 30-gauge needle and a pair of microscissors to completely sever the dorsal and dorsolateral corticospinal tracts (CSTs). We passed a marked needle across the dorsal part of the spinal cord several times to assure that the lesion was at a depth of 1.0 mm. We sutured the muscle layers over the laminectomies and closed the skin on the back with surgical staples. To trace the corticospinal tracts, we made a burr hole overlying cerebral cortex on the right side into the skull 14 days after spinal cord injury. We applied the tracer BDA (MW 10,000, 10% in PBS) (Molecular Probes, Eugene, Oreg.) to 4 injection sites at a depth of 0.7 mm from the cortical surface. Four weeks after injury, the mice were perfused transcardially with PBS, followed by 4% paraformaldehyde. Mice used for sNogoR310 expression experiments did not receive any tracer injection.

For the mice used for western blot analysis, the spinal cord at a level between T3 and L3 was collected without perfusion 14 days after injury. Mice used for Nogo receptor-1 immunohistochemical staining were perfused with 4% paraformaldehyde 10 days after hemisection, and the injured spinal cord was removed for sectioning. To examine sNogoR310 expression in the injured brain of transgenic and WT mice, a cortex stab injury was performed with a number 11 scalpel blade held in a stereotaxic apparatus (David Kopf, Tujunga, Calif.). A 4 mm parasagittal cut was made, 0.5 mm posterior to Bregma, 1.5 mm laterally from midline and 3.5 mm deep.

We detected increased levels of sNogoR310 in soluble extracts of spinal cords ten days after the injury in transgenic mice but not in WT mice, consistent with the upregulation after injury of GFAP around the lesion. To confirm that this was not due to compensatory upregulation of Nogo-A, we tested its expression and found that it was similar in either intact or injured cortex and spinal cord from either WT and transgenic mice.

We examined the cellular expression of sNogoR310 in injured CNS by immunostaining the injured brain and spinal cord containing the lesion area with antibodies against Nogo receptor-1 and GFAP. The general morphology of reactive astrocytic glia does not differ between WT and transgenic mice, but the density stained for Nogo receptor-1 in both intra- and extracellular space is remarkably higher in the gfap::sNogoR310 transgenic mice than in WT mice, indicating increased sNogoR310 expression around the lesion in transgenic mice. Nogo receptor-1 protein is co-localized with astrocytic marker GFAP only in the transgenic mice. There is also a greatly enhanced diffuse non-cellular staining in the transgenic samples, consistent with sNogoR310 in the extracellular space. Neuronal cell body Nogo receptor-1 staining is detected in both WT and transgenic mice.

EXAMPLE 16

Secreted sNogoR310 Induces CST Sprouting in Transgenic Mice

We tested whether increased expression of sNogoR310 around the lesion in transgenic mice results in the regeneration of injured axons.

We investigated the integrity of descending corticospinal tracts (CST) by injecting anterograde tracer biotin dextran amine (BDA) into the right motor cortex as described in Li and Strittmatter, 2003, J. Neurosci., 23, 4219-27. In littermate WT mice, the prominent dorsal CST (dCST) is tightly bundled rostral to the lesion, and a few dorsolateral CST fibers are visible ipsilaterally. A small number of BDA-labeled short collateral sprouts project into gray matter, particularly in the ventral cord, but the sprouting is largely confined to the side of the cord contralateral to the tracer injection. However, the sections rostral to dorsal hemisection from injured sNogoR310 transgenic mice indicate a quite different BDA labeling pattern. A high density of BDA-labeled CST fibers are observed outside of prominent dCST in all the transgenic mice from line Tg08 or line Tg01. Ectopic fibers extend throughout the gray matter area, and some fibers reach into lateral and dorsolateral white matter. Several fibers (4-12 sprouts per transverse section) are seen on the opposite side of the spinal cord (ipsilateral to the tracer injection site). Micro densitometric measurement of the collateral sprouts indicates approximately a tenfold increase in sprouting density in sNogoR310 transgenic mice. Examination of parasagittal longitudinal sections from 1 to 4 mm rostral to the lesion reveals that dCST fibers extend a large number of branching sprouts into the ventral gray matter area in sNogoR310 transgenic mice, in contrast to the littermate WT animals. Generally, the pattern and extent of sprouting rostral to the lesion in transgenic mice are similar to those observed in the mice treated systemically with Nogo receptor-1 antagonist peptide NEP1-40 (Li and Strittmatter, 2003).

These results demonstrate that secreted sNogoR310 induces CST sprouting in the transgenic mice.

EXAMPLE 17

Regenerating CST Axons Bypass the Lesion Site into Distal Spinal Cord in sNogoR310 Transgenic Mice We isolated spinal cord 4 mm rostral to and 4 mm caudal to the lesion site (8 mm long in total) from transgenic mice and embedded it in a glutaraldehyde-polymerized albumin matrix, and cut parasagittally on a vibratome (30 μm thick). We collected transverse sections (50 μm) from the spinal cord 5-7 mm rostral to and 5-7 mm caudal to the injury site. For sNogoR310-Fc injection experiments in rats, the spinal cord extending from 10 mm rostral to 10 mm caudal from the lesion site was cut parasaggitally (50 μm) on a vibrating microtome. Transverse sections were collected from the spinal cord 11-16 mm rostral to and 11-16 mm caudal to the injury site. We incubated the sections with avidin-biotin-peroxidase complex and visualized the BDA tracer by nickel-enhanced diaminobenzidine HRP reaction (Grandpre, 2002, Nature, 417, 547-551). We processed some sections for serotonin immunohistochemistry (anti-5-HT antibody) by indirect immunofluoresence. To visualize the lesion area, we double-stained some sections with antibodies directed against GFAP (Sigma®, St. Louis, Mo.). We mounted, dehydrated and covered the sections with mounting medium.

We tested whether the fibers induced by sNogoR310 expressed in transgenic mice after injury (see Example 16) cross the lesion area into the caudal spinal cord to provide functional recovery.

Consecutive parasaggital sections across the injury site drawn in camera lucida display the overall distribution pattern of the regenerating CST fibers a few millimeters from the lesion. Sections from WT mice show no CST fibers extending beyond the injury site. Similar sections from sNogoR310 transgenic mice display numerous CST fibers that cross the transection area and project into the distal gray and white matter areas in a highly branched pattern. Immediately rostral to hemisection, a high density of BDA-labeled CST sprouting originated from prominent dCST projects into the lesion area, but most CST sprouts failed to pass the transection area where scar formation and tissue cavitation are prominent. A small but highly significant fraction of the regenerating axons bypass the lesion site through the remaining tissue bridges of the ventral and ventrolateral gray and white matter. In addition, a few CST fibers appear to cross the transection area itself via the lesioned dorsal and dorsolateral spinal cord into distal regions. In the vicinity of lesion, the course of regenerating fibers was typically tortuous and quite distinct from the normal straight fibers in the rostral CST. Collaterals and arborized fibers are most frequently seen in gray matter area of distal spinal cord. The reconstructions demonstrate 5-15 BDA-labeled regenerating fibers coursing in the rostral-caudal axis at any level 1-4 mm caudal to the lesion in each transgenic mouse. For transverse sections 5-7 mm caudal to dorsal hemisection, BDA-labeled CST axons are seen in both the gray matter and white matter areas in each transgenic mouse. The fiber counts for the transgenic mice indicate approximately a similar number of BDA-labeled CST fibers to the proximal levels in the sagittal sections.

In addition to CST fibers, the other descending tracts, such as raphespinal fibers, also contribute to locomotor function in mice. In this mouse dorsal over-hemisection model, the transection injures a majority of the serotonergic fibers, decreasing the density of these fibers by approximately 80% in the ventral horn. Analysis of total length of serotonin fibers in the ventral horn of caudal spinal cord indicates a much greater number of these fibers in transgenic mice than WT group, indicating that the growth-promoting effects of sNogoR310 in transgenic mice are not limited to one axon descending pathway.

EXAMPLE 18

Transgenic Expression of sNogoR310 Improves Locomotor Recovery

The CST axon tracing and serotonergic fiber analysis indicate that the sNogoR310 released from astrocytes in transgenic mice stimulates extensive anatomical regeneration of injured descending axons in the spinal cord. We performed several behavioral tests as described in Example 12 to determine whether these regenerated fibers benefit functional recovery.

Figure 13A:
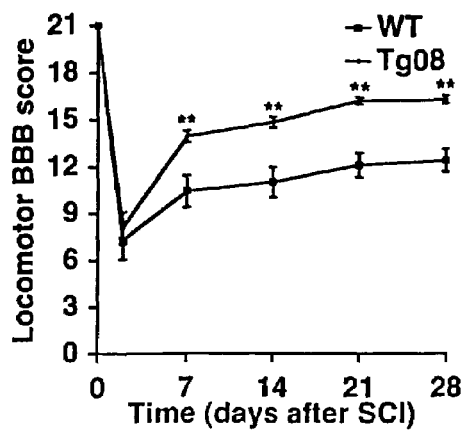
FIGS. 13A and 13B report the locomotor BBB score as a function of time after dorsal hemisection in the WT or transgenic mice from Line 08 or Line 01.
Figure 13B:
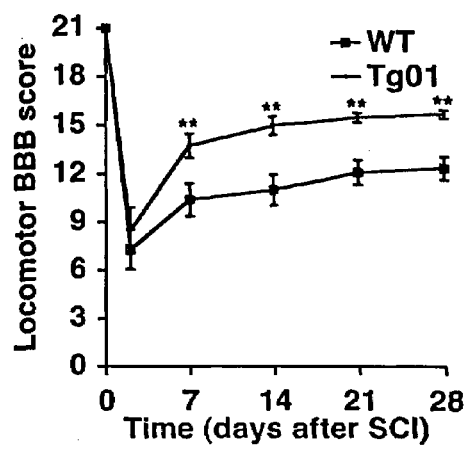

As assessed by the BBB test, the WT mice partially recover locomotor function during a 4-week period of survival. At 4 weeks post-injury, most WT mice recover a level characterized by consistent plantar stepping with consistent weight support, but they exhibit only occasional to frequent forelimb-hindlimb coordination, with a rotation of predominant paw position when making initial contact with surface. In contrast, the BBB scores of sNogoR310 transgenic mice from both lines Tg08 and Tg 01 are significantly higher than control group throughout the 7-28 day observation period (FIGS. 13A and 13B). At 28 days after injury, most transgenic mice show consistent forelimb-hindlimb coordination, and the predominant paw position is parallel to the body.

Figure 13C:
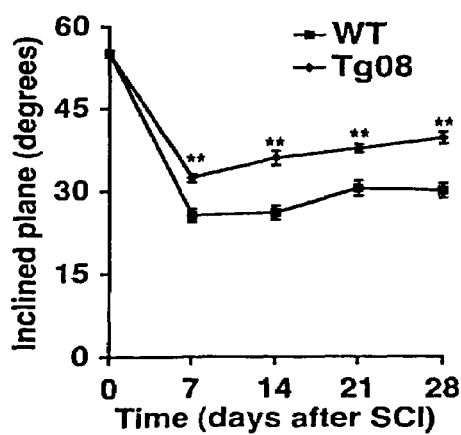
FIG. 13C graphs the maximal tolerated inclined plane angle as a function of time after injury for WT and transgenic mice.
Figure 13D:
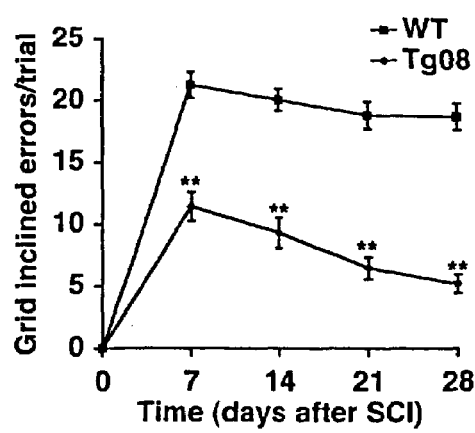
FIG. 13D shows hindlimb errors during inclined grid climbing as a function of post-injury time. In all the graphs, means±s.e.m. from 7-9 mice in each group are reported. The values from transgenic group are statistically different from the WT mice. (double asterisks, P<0.01; Student's t-test).

We employed two more behavioral tests to further characterize the performance of sNogoR310 transgenic mice. First, we measured the maximal angle to which a board would be tilted without a mouse losing its grip within 5 sec. Before dorsal hemisection injury, both transgenic and WT mice can sustain their posture on board angled at 55 degrees. On days 7-28 after injury, the sustainable angle is reduced in all mice, but the angles sustainable by the transgenic mice are significantly greater than those for the control group (FIG. 13C). In another behavioral test, mice climbed a grid placed at a 45 degree angle to vertical and excursions of the hindlimbs below the plane of the grid were counted (Metz et al., 2000). No mice made errors on this test during the pre-injury training. There are numerous foot fault errors with only minimal improvement in WT mice during the period 2-6 weeks post-injury. In contrast, the sNogoR310 transgenic mice exhibit a progressive improvement in grid climbing during this period, with the majority of improvement occurring between 1-3 weeks post-injury (FIG. 13D). Thus, transgenic mice secreting sNogoR310 from astrocytes exhibit CST regeneration, raphespinal sprouting and improved motor function after thoracic spinal hemisection.

EXAMPLE 19

Intrathecal Administration of sNogoR310-Fc Protein Induces CST Sprouting

As a second test of the growth-promoting benefit of soluble Nogo receptor-1 after spinal trauma, we administered the purified protein intrathecally.

We fused the ligand binding domain (27-310) of rat Nogo receptor-1 to the rat IgG1 Fc domain to promote stability and purification. We purified protein from stably transfected CHO cells. This protein blocks Nogo-66, MAG and myelin action in vitro, as shown previously for mouse sNogoR310-Myc His (Fournier et al., 2002, J. Neurosci., 22, 8876-8883; Liu et al., 2002, Science, 297, 1190-1193). We delived sNogoR310-Fc protein intrathecally to rats with a mid-thoracic dorsal hemisection injury through an osmotic minipump. During a four-week survival period after injury, 1.2 mg sNogoR310-Fc protein was locally administered in each rat. In rats receiving the vehicle treatment (1.2 mg rat IgG), sections rostral to hemisection display the tightly bundled prominent dorsal CST and very few ectopic BDA-labeled CST fibers above the lesion site. Sections rostral to lesion from injured rats receiving sNogoR310-Fc protein exhibit a quite different pattern of labeling. Numerous ectopic fibers sprouting from the BDA-labeled CST are observed from transverse and parasagittal sections. In some cases, projections cross from the dCST area near the midline to the circumference of the cord, becoming intermingled with the dorsolateral CST. The sprouting axons extend through gray matter to a greater extent than white matter. A measure of ectopic sprouting fibers ($\geqq 100$ μm in transverse sections, $\geqq 200$ μm in sagittal sections) adjacent to the dCST reveals a greater increase in the sNogoR310-Fc-treated rats.

EXAMPLE 20

CST Axons Regenerate into Distal Spinal Cord in sNogoR310-Fc Treated Rats

We deeply anaesthetized female Sprague-Dawley rats (190-250 g) and conducted laminectomies at spinal levels of T6-7, exposing the spinal cord. We cut the dorsal half of the spinal cord with a 30-gauge needle and a pair of microscissors to sever the dorsal parts of CSGT tracts, and assured the depth of the lesion (1.8 mm) by passing the sharp part of a number 11 blade across the dorsal half of the cord (Grandpre et al., 2002, Nature, 417, 547-551). An osmotic minipump (Alzet® 2ML4, 2 ml volume, 2.5 μl/h, 28 day delivery), which was filled with 1.2 mg rat IgG in PBS or 1.2 mg sNogoR310-Fc fusion protein in PBS, was sutured to muscles under the skin on the back of the animals. A catheter connected to the outlet of the minipump was inserted into the intrathecal space of the spinal cord at the T7-8 level through a small hole in the dura.

Nogo receptor-1 antagonist protein infusion induced extensive sprouting rostral to a rat hemisection, but a more critical issue is whether the sprouting CST fibers project to distal spinal cord and contribute to locomotor recovery. Longitudinal sections across lesion site from vehicle-treated rats display no detectable or a very small number of BDA-labeled ventral CST fibers below the lesion level (GrandPre et al., 2002; Weidner et al., 2001, Proc. Natl. Acad. Sci. USA, 98, 3513-3518). The similar sections from sNogoR310-Fc treated rats demonstrate many BDA-labeled fibers bypass the transection site and project to the caudal spinal cord largely through the bridging tissues of the ventral and ventrolateral spinal cord. Immunostaining for astrocytic marker GFAP display that the extent of transection reached deeper than central canal area. Unlike the linear profile of rostral fibers in prominent dorsal CST, the regenerated CST fibers usually follow a highly branching trajectory in the distal spinal cord, particularly in gray matter area. These fibers are detected in many regions of spinal cord, but they are more easily seen in the central part and dorsal half of spinal cord throughout the spinal cord. Counts of CST fibers from sagittal sections indicate approximately 20 BDA-labeled axons at 1-2 mm caudal to lesion and 15 traced axons at 7-8 mm distal to lesion from each sNogoR310-Fc-treated rat.

Generally, the branching pattern of these fibers is similar to that observed from local NEP 1-40 peptide treated animals, but more collateral branching in each sprout is seen from the sections treated with sNogoR310-Fc protein. A measure of the sprouts from distal spinal cord demonstrates that the total collateral length of each sprout in sNogoR310-Fc-treated rats is twice as great as that from NEP 1-40-treated animals. The number of sprouts ($\geqq 200$ μm in length) at 1-10 mm caudal to spinal cord in both Nogo receptor-1 antagonist-treated groups is approximately 20-40 times greater than control groups. More sprouts are seen from sNogoR310-Fc treated rats than local NEP 1-40 treatment (~50 vs. 25 sprouts/rat), but this difference is not statistically significant ($p=0.1713$, t-test).

Regenerating CST axons are observed in transverse sections of spinal cord 11-15 mm caudal to hemisection in rats receiving sNogoR310-Fc treatment. These fibers are detected in both gray matter and white matter of the spinal cord. The fibers detected in gray matter often exhibit more collateral branching than in white matter area. In contrast, in transverse sections from vehicle-treated group, only occasional BDA-labeled are seen in the ventral white matter area, consistent with the uninjured ventral CST axons. At this level of distal spinal cord, the average number of BDA-labeled CST fibers from both Nogo receptor-1 antagonist-treated groups [sNogoR310-Fc and NEP 1-40] are approximately 20-fold greater than vehicle-treated rats. Taken together, both Nogo receptor antagonists, sNogoR310-Fc protein and NEP 1-40 peptide, result in dramatic CST axon regeneration in distal spinal cord, but the sprouting induced by the former exhibits a more highly branched pattern.

EXAMPLE 21

Local sNogoR310-Fc Induces Sprouting of Rubropinal and Serotonergic Axons in Injured Rat Spinal Cord Fourteen days after hemisection, a burr hole was made on each side of the skull overlying the sensorimotor cortex of the lower limbs to trace CST fibers. The anterograde neuronal tracer BDA (10% in PBS, 3.5 μl per cortex) was applied at seven injection sites at a depth of 1.5 mm from dura on each side (Grandpre, 2002). For rubrospinal tract tracing in rats, the tracer BDA (1 μl; MW 10,000; 10% in PBS) was injected into red nucleus on the left side (5.8 mm posterior to bregma, 0.7 mm lateral, 7.0 mm ventral to the skull surface). Two weeks after BDA injection, these animals were perfused with PBS, followed by 4% paraformadehyde, and tissue was collected for histology.

Repair of injured rubrospinal tract (RST) fibers contribute to functional improvements after spinal cord injury (Liu et al., 1999, J. Neurosci., 19, 4370-4387). The widespread distribution of Nogo receptor-1 in CNS neurons (Wang et al., 2002, J. Neurosci., 22, 5505-5515) makes it possible that inhibition of Nogo receptor-1 with its antagonist may result in regrowth of RST axons after injury. To test effects of sNogoR310-Fc on injured RST, the integrity of this pathway was traced by injecting BDA into left red nucleus. At the spinal cord level, RST fibers are normally located in dorsolateral white matter area of spinal cord, and are transected by the dorsal hemisections of this study. In transverse sections 11-15 mm rostral to lesion from control rats, a small number of short BDA-labeled fibers are seen between the prominent RST and dorsal horn gray matter. Sections at same level treated with sNogoR310-Fc exhibit many linking fibers between the main RST and dorsal horn gray matter. Transverse sections 11-15 mm distal to SCI, no BDA-labeled RST fibers in vehicle-treated rats. In contrast, sections at the same level receiving sNogoR310-Fc treatment display many BDA-labeled RST fibers in both gray and white matter contralateral to tracer injection. Some sprouts with a branching pattern are seen in the gray matter ipsilateral to BDA injection.

Ruphespinal spinal fibers were also examined in sNogoR310-Fc treated spinal injured rats. Immunostaining demonstrates the density of serotonergic fibers 11-15 mm rostral to lesion that is similar between vehicle and sNogoR310-Fc treated groups. In the sections 11-15 mm below the lesion, the seroton fibers in sNogoR310-Fc treated rats are twice as numerous as those in the control group. These results demonstrate that the responsiveness to Nogo receptor-1 inhibition by sNogoR310-Fc protein is not limited to CST fibers, and that the other descending tracts, such as rubrospinal and serotonergic axons, are also responsive to Nogo receptor-1 antagonism.

EXAMPLE 22

Local Treatment with sNogoR310-Fc Improves Functional Recovery in Rats

Intrathecal administration of sNogoR310-Fc protein stimulates axon regeneration in several descending pathways after traumatic spinal cord injury. We tested whether the protein also improves functional recovery in the injured spinal cord.

At 2 weeks after the hemisection, the locomotor BBB score in vehicle-treated rats reaches a stable level of 12 (FIG. 14A). At 4 weeks after lesion, most of controls (6 out of 7) have frequent-consistent weight-supported plantar steps and frequent-consistent forelimb-hindlimb coordination, but they have a rotation of predominant paw position when making initial contact with surface. In contrast, in rats receiving sNogoR310-Fc protein treatment, the locomotor score continues to improve between 2-4 weeks post-trauma. At 4 weeks after injury, all 9 of the sNogoR310-Fc treated animals had consistent forelimb-hindlimb coordination and a parallel paw position at initial contact with the testing surface.

Grid walking has been used to assess the deficits in descending fine motor control after spinal cord injury (Metz et al., 2000). This performance requires forelimb-hindlimb coordination and voluntary movement control mediated by ventrolateral, corticospinal and rubrospinal fibers. During the pre-injury training, all the rats accurately place their hindlimbs on the grid bars. At 2-4 weeks post-injury, control rats make 8-9 errors per session with only minimal improvement over time. In contrast, the rats treated with sNogoR310-Fc exhibit a progressive improvement on grid walking and make significant fewer errors (4-7/session on average). The majority of the improvement occurs at 2-3 weeks after injury. Analysis of hindpaw footprints in control group displays that stride length is significantly decreased and stance width is increased at 4 weeks post-hemisection, compared with uninjured rats or injured animals receiving sNogoR310-Fc treatment (FIG. 14C). Therefore, these multiple behavioral tests demonstrate that blockade of Nogo receptor-1 function with local injection of antagonist protein improves locomotor recovery after injury.

Biological Deposits

Hybridomas HB 7E11 (ATCC® accession No. PTA-4587), HB 1H2 (ATCC® accession No. PTA-4584), HB 3G5 (ATCC® accession No. PTA-4586), HB 5B10 (ATCC® accession No. PTA-4588) and HB 2F7 (ATCC® accession No. PTA-4585) were deposited with the American Type Culture Collection ("ATCC®"), 10801 University Boulevard, Manassas, Va. 20110-2209, USA, on Aug. 9, 2002.

As those skilled in the art will appreciate, numerous changes and modifications may be made to the preferred embodiments of the invention without departing from the spirit of the invention. It is intended that all such variations fall within the scope of the invention.

The invention claimed is:

1. An isolated soluble Nogo receptor-1 polypeptide comprising amino acids 26-310 of SEQ ID NO:7 fused to immunoglobulin Fc; wherein said soluble Nogo receptor-1 polypeptide inhibits neurite outgrowth inhibition.

2. The soluble Nogo receptor-1 polypeptide of claim 1 joined to a signal sequence.

3. A composition comprising a pharmaceutically acceptable carrier and the soluble Nogo receptor-1 polypeptide of claim 1.

4. The composition of claim 3 further comprising one or more additional therapeutic agents.

5. The composition of claim 4, wherein said therapeutic agent is an anti-inflammatory agent.

6. The composition of claim 3, wherein said composition is formulated for administration by a route selected from the group consisting of parenteral administration, subcutaneous administration, intravenous administration, intramuscular administration, intraperitoneal administration, and microinfusion administration.

7. A method for inhibiting growth cone collapse of a neuron, comprising contacting the neuron with the soluble Nogo receptor-1 polypeptide of claim 1.

8. A method for decreasing the inhibition of neurite outgrowth or neurite sprouting in a neuron, comprising contacting the neuron with the soluble Nogo receptor-1 polypeptide of claim 1.

9. A method of promoting survival of a neuron at risk of dying, comprising contacting the neuron with an effective amount of the soluble Nogo receptor-1 polypeptide of claim 1.

10. A method of treating diabetic neuropathy in a mammal comprising administering to a mammal in need of said treatment an effective amount of the soluble Nogo receptor-1 polypeptide of claim 1.

11. A method of treating traumatic brain injury in a mammal comprising administering to a mammal in need of said treatment an effective amount of the soluble Nogo receptor-1 polypeptide of claim 1.

12. A method of treating spinal cord injury in a mammal comprising administering to a mammal in need of said treatment an effective amount of the soluble Nogo receptor-1 polypeptide of claim 1.

* * * * *

SEQUENCE LISTING

```
<160> NUMBER OF SEQ ID NOS: 25

<210> SEQ ID NO 1
<211> LENGTH: 16
<212> TYPE: PRT
<213> ORGANISM: Rattus sp.

<400> SEQUENCE: 1

Leu Asp Leu Ser Asp Asn Ala Gln Leu Arg Val Val Asp Pro Thr Thr
1               5                   10                  15

<210> SEQ ID NO 2
<211> LENGTH: 16
<212> TYPE: PRT
<213> ORGANISM: Homo sapiens

<400> SEQUENCE: 2

Leu Asp Leu Ser Asp Asn Ala Gln Leu Arg Ser Val Asp Pro Ala Thr
1               5                   10                  15

<210> SEQ ID NO 3
<211> LENGTH: 35
<212> TYPE: PRT
<213> ORGANISM: Rattus sp.

<400> SEQUENCE: 3

Ala Val Ala Ser Gly Pro Phe Arg Pro Phe Gln Thr Asn Gln Leu Thr
1               5                   10                  15

Asp Glu Glu Leu Leu Gly Leu Pro Lys Cys Cys Gln Pro Asp Ala Ala
            20                  25                  30

Asp Lys Ala
        35

<210> SEQ ID NO 4
<211> LENGTH: 35
<212> TYPE: PRT
<213> ORGANISM: Homo sapiens

<400> SEQUENCE: 4

Ala Val Ala Thr Gly Pro Tyr His Pro Ile Trp Thr Gly Arg Ala Thr
1               5                   10                  15

Asp Glu Glu Pro Leu Gly Leu Pro Lys Cys Cys Gln Pro Asp Ala Ala
            20                  25                  30

Asp Lys Ala
        35
```

<210> SEQ ID NO 5
<211> LENGTH: 10
<212> TYPE: PRT
<213> ORGANISM: Mus musculus

<400> SEQUENCE: 5

Cys Arg Leu Gly Gln Ala Gly Ser Gly Ala
 1               5                  10

<210> SEQ ID NO 6
<211> LENGTH: 344
<212> TYPE: PRT
<213> ORGANISM: Homo sapiens

<400> SEQUENCE: 6

Met Lys Arg Ala Ser Ala Gly Gly Ser Arg Leu Leu Ala Trp Val Leu
 1               5                  10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
    275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

```
Thr Gly Arg Ala Thr Asp Glu Glu Pro Leu Gly Leu Pro Lys Cys Cys
                325                 330                 335

Gln Pro Asp Ala Ala Asp Lys Ala
                340

<210> SEQ ID NO 7
<211> LENGTH: 310
<212> TYPE: PRT
<213> ORGANISM: Homo sapiens

<400> SEQUENCE: 7

Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
                 20                  25                  30

Cys Tyr Asn Glu Pro Lys Val Thr Thr Ser Cys Pro Gln Gln Gly Leu
             35                  40                  45

Gln Ala Val Pro Val Gly Ile Pro Ala Ala Ser Gln Arg Ile Phe Leu
         50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala
305                 310

<210> SEQ ID NO 8
<211> LENGTH: 344
<212> TYPE: PRT
<213> ORGANISM: Rattus sp.
```

<400> SEQUENCE: 8

```
Met Lys Arg Ala Ser Ser Gly Gly Ser Arg Leu Pro Thr Trp Val Leu
  1               5                  10                  15

Trp Leu Gln Ala Trp Arg Val Ala Thr Pro Cys Pro Gly Ala Cys Val
             20                  25                  30

Cys Tyr Asn Glu Pro Lys Val Thr Thr Ser Arg Pro Gln Gln Gly Leu
         35                  40                  45

Gln Ala Val Pro Ala Gly Ile Pro Ala Ser Ser Gln Arg Ile Phe Leu
     50                  55                  60

His Gly Asn Arg Ile Ser Tyr Val Pro Ala Ala Ser Phe Gln Ser Cys
 65                  70                  75                  80

Arg Asn Leu Thr Ile Leu Trp Leu His Ser Asn Ala Leu Ala Gly Ile
                 85                  90                  95

Asp Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
            115                 120                 125

Leu Gly His Leu His Thr Leu His Leu Asp Arg Cys Gly Leu Gln Glu
        130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Gly Val Pro Ser Asn
        275                 280                 285

Leu Pro Gln Arg Leu Ala Gly Arg Asp Leu Lys Arg Leu Ala Thr Ser
    290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala
            340
```

<210> SEQ ID NO 9
<211> LENGTH: 310
<212> TYPE: PRT
<213> ORGANISM: Rattus sp.

<400> SEQUENCE: 9

```
Met Lys Arg Ala Ser Ser Gly Gly Ser Arg Leu Pro Thr Trp Val Leu
  1               5                  10                  15
```

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
            115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
    290                 295                 300

Asp Leu Glu Gly Cys Ala
305                 310

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 19
<212> TYPE: PRT
<213> ORGANISM: Rattus sp.

<400> SEQUENCE: 11

```
Arg Val His Pro His Ala Phe Arg Asp Leu Gly Arg Leu Met Thr Leu
 1               5                  10                 15

Tyr Leu Phe

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 12
tgaggagacg gtgaccgtgg tcccttggcc ccag                              34

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 13
ggggatatcc accatgaagt tgcctgttag gctgttg                           37

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Degenerate
      primer

<400> SEQUENCE: 14
ggggatatcc accatgaggk ccccwgctca gytyctkgga                        40

<210> SEQ ID NO 15
<211> LENGTH: 144
<212> TYPE: PRT
<213> ORGANISM: Artificial Sequence
<220> FEATURE:
<223> OTHER INFORMATION: Description of Artificial Sequence: Synthetic
      light chain peptide sequence

<400> SEQUENCE: 15

Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Asp Ala Glu Asp Leu Gly Val Tyr Phe Cys
            100                 105                 110

Ser Gln Ser Thr His Val Pro Phe Thr Phe Gly Gly Gly Thr Lys Leu
        115                 120                 125

Glu Ile Lys Arg Ala Asp Ala Ala Pro Thr Val Ser Ile Ser His His
```

```
            130                 135                 140

<210> SEQ ID NO 16
<211> LENGTH: 144
<212> TYPE: PRT
<213> ORGANISM: Artificial Sequence
<220> FEATURE:
<223> OTHER INFORMATION: Description of Artificial Sequence: Synthetic
      light chain peptide sequence

<400> SEQUENCE: 16

Met Lys Leu Pro Val Arg Leu Leu Val Leu Met Phe Trp Ile Pro Ala
  1               5                  10                  15

Ser Ser Ser Asp Val Val Met Thr Gln Thr Pro Leu Ser Leu Pro Val
             20                  25                  30

Ser Leu Gly Asp Gln Ala Ser Ile Ser Cys Arg Ser Ser Gln Ser Leu
         35                  40                  45

Val His Ser Asn Gly Tyr Thr Tyr Leu His Trp Tyr Leu Gln Arg Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Asp Ala Glu Asp Leu Gly Val Tyr Phe Cys
            100                 105                 110

Ser Gln Ser Thr His Val Pro Tyr Thr Phe Gly Gly Gly Thr Lys Leu
            115                 120                 125

Glu Ile Lys Arg Ala Asp Ala Ala Pro Thr Val Ser Ile Ser His His
        130                 135                 140

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      heavy chain peptide sequence

<400> SEQUENCE: 17

Val Gln Leu Gln Glu Ser Gly Ala Glu Leu Val Met Pro Gly Ala Ser
  1               5                  10                  15

Val Lys Met Ser Cys Lys Ala Ser Gly Tyr Thr Phe Thr Asp Tyr Trp
             20                  25                  30

Met His Trp Val Lys Gln Arg Pro Gly Gln Gly Leu Glu Trp Ile Gly
         35                  40                  45

Ala Ile Asp Pro Ser Asp Ser Tyr Ser Tyr Asn Gln Asn Phe Lys
     50                  55                  60

Gly Lys Ala Thr Leu Thr Val Asp Gly Ser Ser Ser Thr Ala Tyr Met
 65                  70                  75                  80

Gln Leu Ser Ser Leu Thr Ser Glu Asp Ser Ala Val Tyr Tyr Cys Ala
                 85                  90                  95

Arg Arg Ile Thr Glu Ala Gly Ala Trp Phe Ala Tyr Trp Gly Gln Gly
            100                 105                 110

Thr Thr Val Thr
            115

<210> SEQ ID NO 18
<211> LENGTH: 114
<212> TYPE: PRT
```

-continued

```
<213> ORGANISM: Artificial Sequence
<220> FEATURE:
<223> OTHER INFORMATION: Description of Artificial Sequence: Synthetic
      heavy chain peptide sequence
<220> FEATURE:
<221> NAME/KEY: MOD_RES
<222> LOCATION: (3)
<223> OTHER INFORMATION: Variable amino acid

<400> SEQUENCE: 18

Leu Gln Xaa Ser Gly Ala Glu Ile Val Met Pro Gly Thr Ala Val Thr
 1               5                  10                  15

Met Ser Cys Lys Ala Ser Gly Tyr Thr Phe Thr Asp Phe Trp Met His
                20                  25                  30

Trp Val Lys Gln Arg Pro Gly Gln Gly Leu Glu Trp Ile Gly Ala Ile
            35                  40                  45

Asp Pro Ser Asp Ser Tyr Ser Arg Ile Asn Gln Lys Phe Lys Gly Lys
        50                  55                  60

Ala Thr Leu Thr Val Asp Glu Ser Ser Ser Thr Ala Tyr Met Gln Leu
 65                  70                  75                  80

Ser Ser Leu Thr Ser Glu Asp Ser Ala Val Tyr Tyr Cys Ala Arg Arg
                85                  90                  95

Ile Thr Glu Ala Gly Ala Trp Phe Ala Tyr Trp Gly Gln Gly Thr Thr
            100                 105                 110

Val Thr

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain peptide sequence

<400> SEQUENCE: 19

Gly Phe Ser Leu Ser Thr Ser Gly Gly Ser Val Gly
 1               5                  10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain peptide sequence

<400> SEQUENCE: 20

Leu Ile Tyr Ser Asn Asp Thr Lys Tyr Tyr Ser Thr Ser Leu Lys Thr
 1               5                  10                  15

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain peptide sequence
```

```
<400> SEQUENCE: 21

Ser Arg Phe Trp Thr Gly Glu Tyr Asp Val
  1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain peptide sequence

<400> SEQUENCE: 22

Arg Ala Ser Gln Asn Ile Ala Ile Thr Leu Asn
  1               5                  10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain peptide sequence

<400> SEQUENCE: 23

Leu Ala Ser Ser Leu Gln Ser
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      light chain peptide sequence

<400> SEQUENCE: 24

Gln Gln Tyr Asp Asn Tyr Pro Leu
  1               5

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Degenerate
      primer

<400> SEQUENCE: 25
aggtsmarct gcagsagtcw gg                                              22
```